United States Patent [19]

Matsuo et al.

[11] Patent Number: 5,633,232

[45] Date of Patent: *May 27, 1997

[54] TACHYKININ ANTAGONIST DIPEPTIDES

[75] Inventors: Masaaki Matsuo, Toyonaka; Daijiro Hagiwara, Moriguchi; Hiroshi Miyake, Kyoto, all of Japan

[73] Assignee: Fujisawa Pharmaceutical Co., Ltd., Osaka, Japan

[*] Notice: The term of this patent shall not extend beyond the expiration date of Pat. No. 5,164,372.

[21] Appl. No.: 258,456

[22] Filed: Jun. 10, 1994

Related U.S. Application Data

[63] Continuation of Ser. No. 871,723, Apr. 21, 1992, Pat. No. 5,420,297, which is a continuation-in-part of Ser. No. 770,866, Oct. 4, 1991, abandoned.

[30] Foreign Application Priority Data

Oct. 24, 1990 [GB] United Kingdom ............... 9023116

[51] Int. Cl.⁶ .................................................. A61K 38/05
[52] U.S. Cl. ........................... 514/19; 548/532; 548/535; 562/445
[58] Field of Search ............................... 548/525, 535; 562/445; 514/18, 19

[56] References Cited

U.S. PATENT DOCUMENTS

| | | | |
|---|---|---|---|
| 5,164,372 | 11/1992 | Matsuo et al. | 514/19 |
| 5,187,156 | 2/1993 | Matsuo et al. | 514/18 |
| 5,321,032 | 6/1994 | Matsuo et al. | 514/308 |

Primary Examiner—David Lukton
Attorney, Agent, or Firm—Oblon, Spivak, McClelland, Maier & Neustadt, P.C.

[57] ABSTRACT

Disclosed herein are compounds of the following formula:

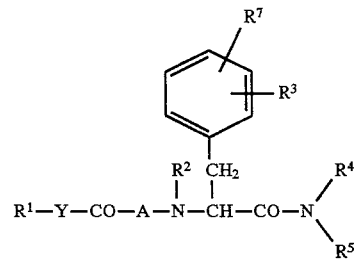

wherein $R^1$ is a group of the formula

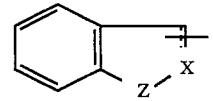

"X" is $CH_2$ or N, "Z" is O, S, or $N-R^6$, "A" is an amino acid residue, and Y, $R^2$, $R^3$, $R^4$, $R^5$, $R^6$, and $R^7$ are substituent variables as defined herein.

The compounds are antagonists of tachykinin, and as such are useful for alleviation of pain and for treatment of disorders including asthma, bronchitis, rhinitis, conjunctivitis, dermatitis, arthritis, and urticaria.

14 Claims, No Drawings

TACHYKININ ANTAGONIST DIPEPTIDES

This is a continuation of application Ser. No. 07/871,723, filed on Apr. 21, 1992 now U.S. Pat. No. 5,420,297, which is a CIP of Ser. No. 07/770,866, filed on Oct. 4, 1991 now abandoned.

The present invention relates to new peptide compounds and pharmaceutically acceptable salt thereof.

More particularly, it relates to new peptide compounds and pharmaceutically acceptable salts thereof which have pharmacological activities such as tachykinin antagonism, especially substance P antagonism, neurokinin A antagonism, neurokinin B antagonism, and the like, to processes for preparation thereof, to pharmaceutical composition comprising the same, and to a use of the same as a medicament.

One object of the present invention is to provide new and useful peptide compounds and pharmaceutically acceptable salts thereof which have pharmacological activities such as tachykinin antagonism, especially substance P antagonism, neurokinin A antagonism, neurokinin B antagonism, and the like.

Another object of the present invention is to provide processes for the preparation of said peptide compounds and salts thereof.

A further object of the present invention is to provide a pharmaceutical composition comprising, as an active ingredient, said peptide compounds and pharmaceutically acceptable salts thereof.

Still further object of the present invention is to provide a use of said peptide compound or a pharmaceutically acceptable salt thereof as tachykinin antagonist, especially substance P antagonist, neurokinin A antagonist or neurokinin B antagonist, useful for treating or preventing tachykinin mediated diseases, for example, respiratory diseases such as asthma, bronchitis, rhinitis, cough, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g., migraine, headache, toothache, cancerous pain, back pain, etc.); and the like in human being or animals.

The object compounds of the present invention can be represented by the following general formula (I).

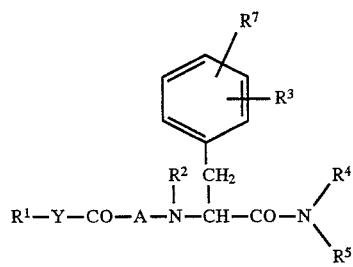

wherein $R^1$ is lower alkyl, aryl, arylamino, pyridyl, pyrrolyl, pyrazolopyridyl, quinolyl, or a group of the formula:

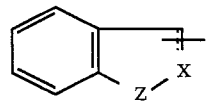

wherein the symbol of a line and dotted line is a single bond or a double bond,

X is CH or N, and

Z is O, S or NH, each of which may have suitable substituent(s);

$R^2$ is hydrogen or lower alkyl;

$R^3$ is suitable substituent excepting hydroxy;

$R^4$ is lower alkyl which may have suitable substituent(s), and $R^5$ is ar(lower)alkyl which may have suitable substituent(s) or pyridyl(lower)alkyl, or $R^4$ and $R^5$ are linked together to form benzene-condensed lower alkylene;

$R^7$ is hydrogen or suitable substituent;

A is an amino acid residue excepting D-Trp, which may have suitable substituent(s); and Y is bond, lower alkylene or lower alkenylene.

According to the present invention, the new peptide compounds (I) can be prepared by processes which are illustrated in the following schemes.

Process 1

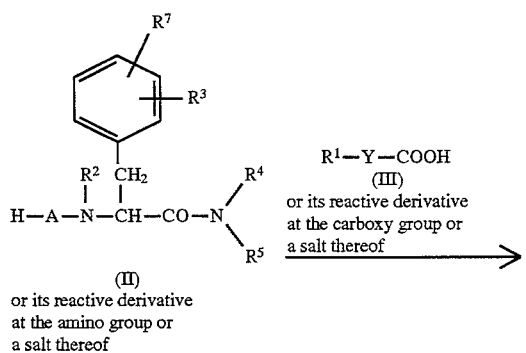

-continued
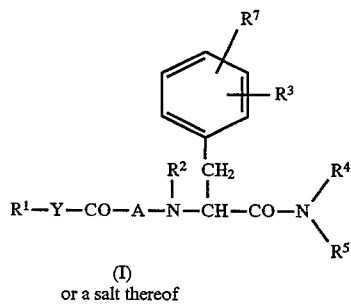
(I)
or a salt thereof
Process 2
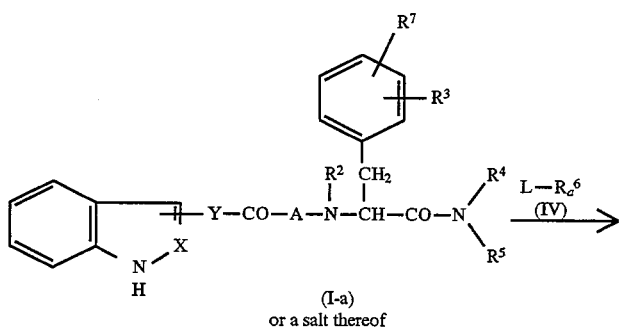
(I-a)
or a salt thereof
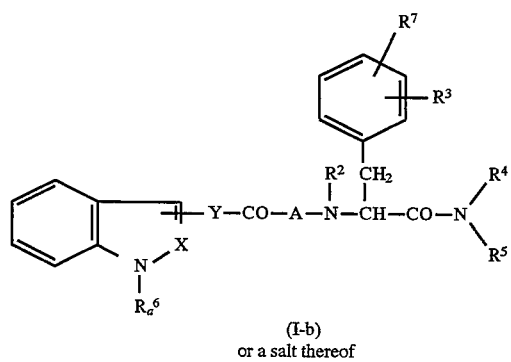
(I-b)
or a salt thereof
Process 3
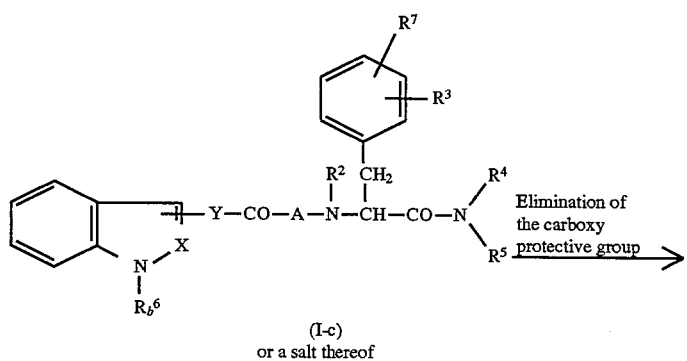
(I-c)
or a salt thereof -continued
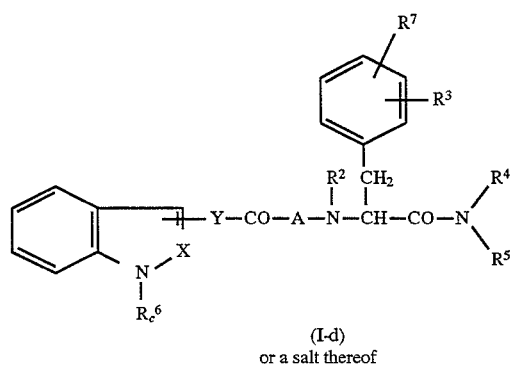
(I-d)
or a salt thereof
Process 4
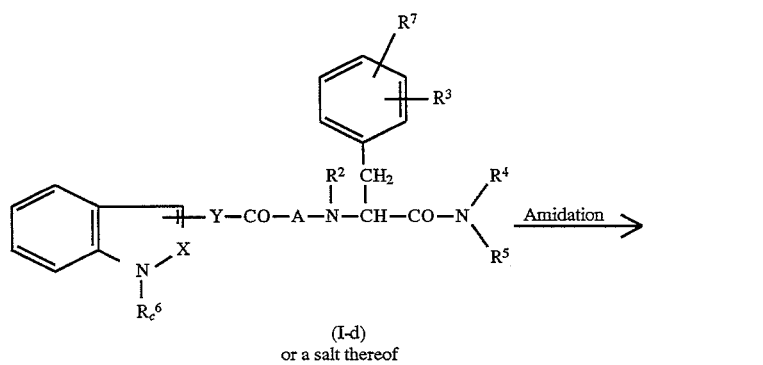
(I-d)
or a salt thereof
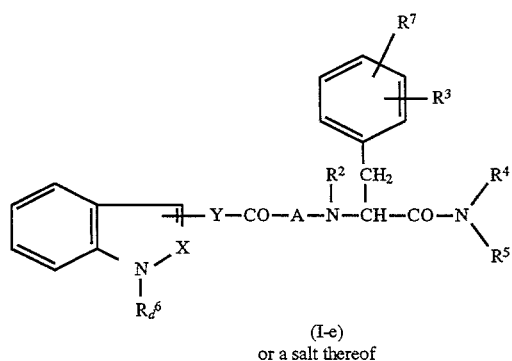
(I-e)
or a salt thereof
Process 5
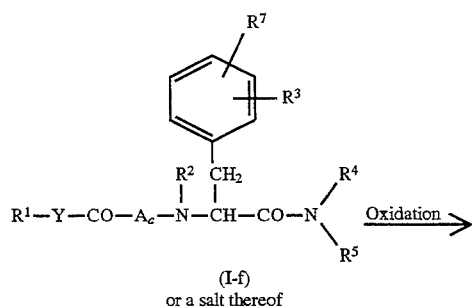
(I-f)
or a salt thereof -continued
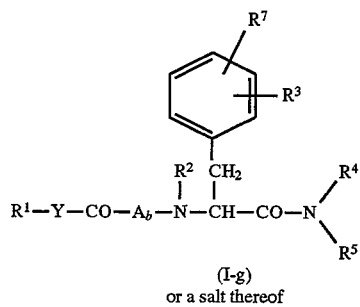
(I-g)
or a salt thereof
Process 6
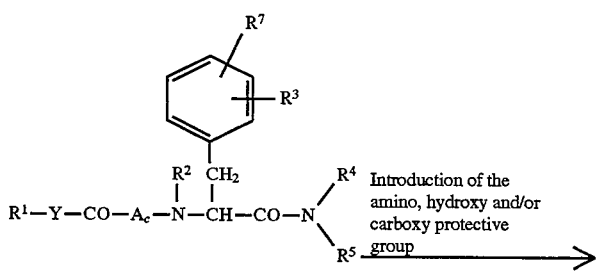 Introduction of the amino, hydroxy and/or carboxy protective group →
(I-h)
or its reactive derivative at the
amino, hydroxy and/or carboxy group
or a salt thereof
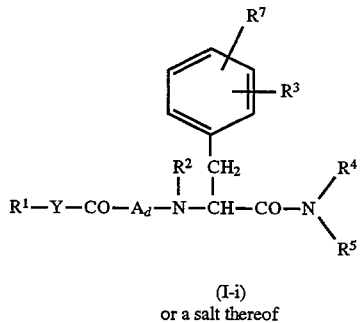
(I-i)
or a salt thereof
Process 7
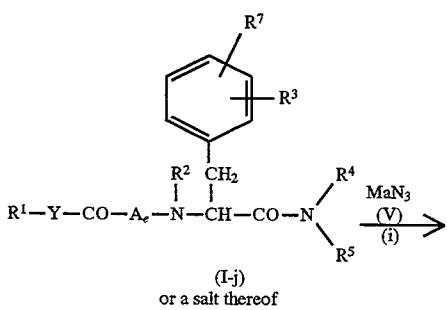 $\xrightarrow{\text{MaN}_3 \atop (V) \atop (i)}$
(I-j)
or a salt thereof -continued
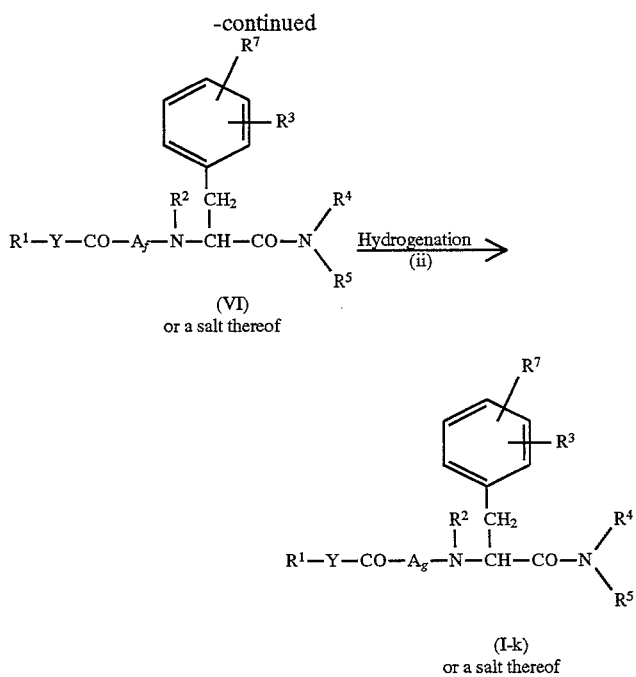
(VI)
or a salt thereof
(I-k)
or a salt thereof
Process 8
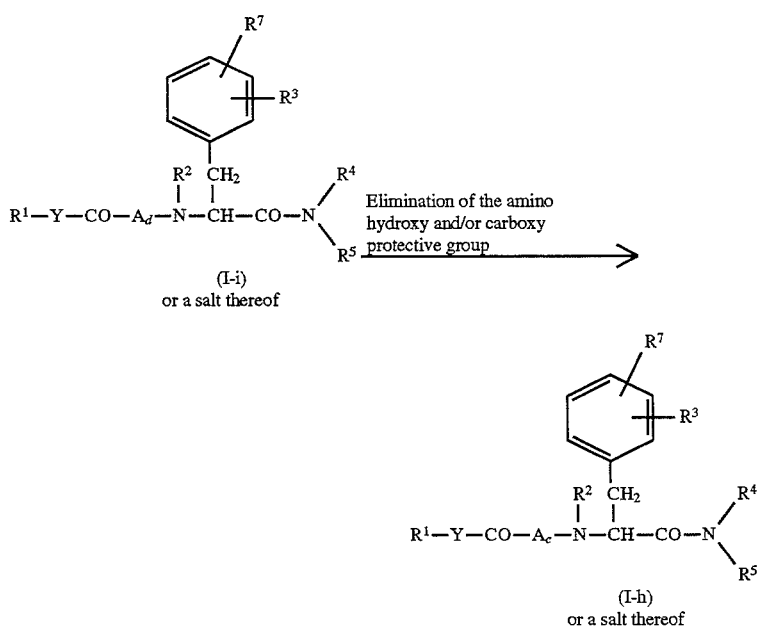
(I-i)
or a salt thereof
(I-h)
or a salt thereof
Process 9
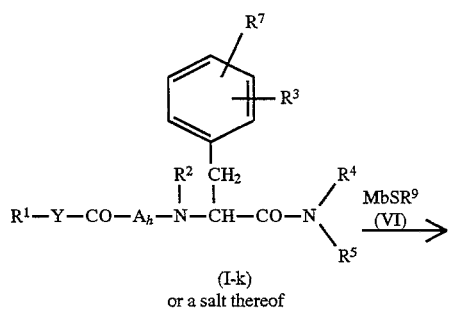
(I-k)
or a salt thereof -continued
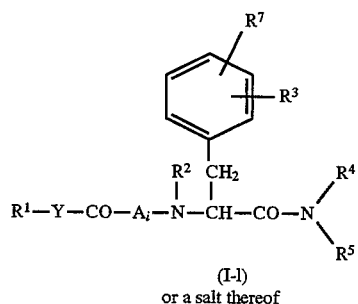
(I-l)
or a salt thereof
Process 10
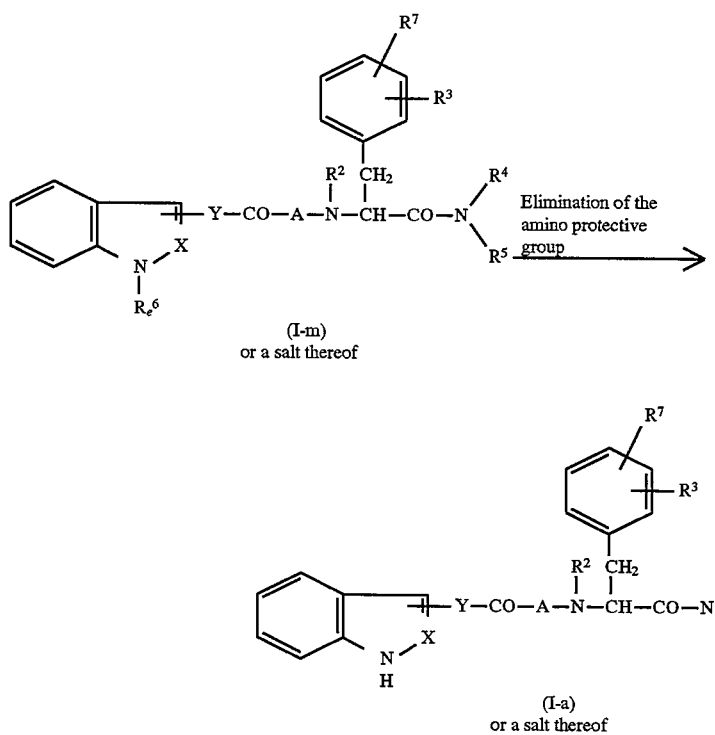
(I-m)
or a salt thereof
Elimination of the amino protective group →
(I-a)
or a salt thereof
Process 11
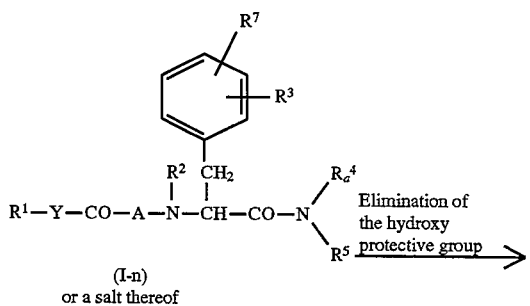
(I-n)
or a salt thereof
Elimination of the hydroxy protective group →

-continued
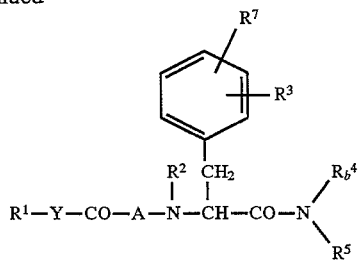
(I-o)
or a salt thereof
Process 12
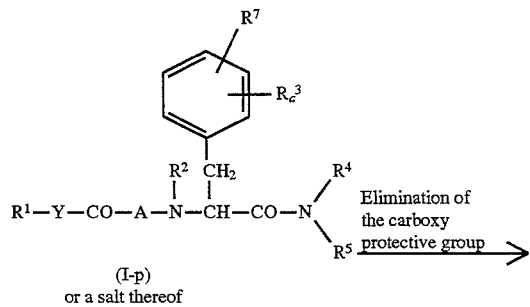
(I-p)
or a salt thereof
Elimination of
the carboxy
protective group
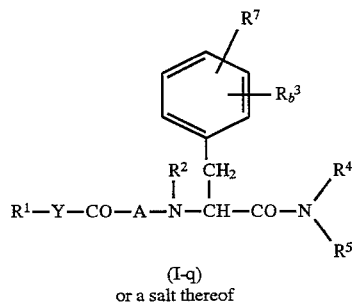
(I-q)
or a salt thereof
Process 13
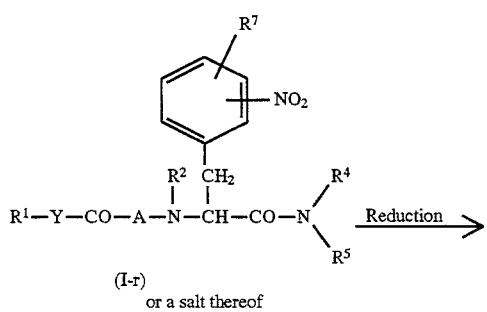
(I-r)
or a salt thereof
Reduction
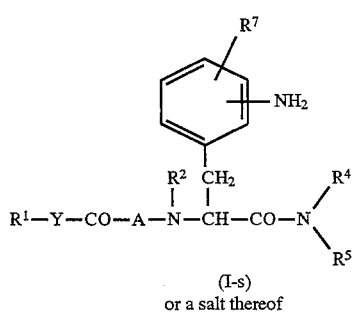
(I-s)
or a salt thereof wherein $R^1$, $R^2$, $R^3$, $R^4$, $R^5$, $R^7$, A, X and Y are each as defined above, $R_a^3$ is protected carboxy(lower)alkoxy, $R_b^3$ is carboxy(lower)alkoxy, $R_a^4$ is protected hydroxy(lower)alkyl, $R_b^4$ is hydroxy(lower)alkyl, $R_a^6$ is lower alkyl which may have suitable substituent(s), $R_b^6$ is protected carboxy(lower)alkyl, $R_c^6$ is carboxy(lower)alkyl, $R_d^6$ is carbamoyl(lower)alkyl which may have suitable substituent(s), $R_e^6$ is amino protective group, $R^9$ is lower alkyl, $A_a$ is an amino acid residue containing a thio, $A_b$ is an amino acid residue containing a sulfinyl or sulfonyl, $A_c$ is an amino acid residue containing an amino, a hydroxy and/or a carboxy, $A_d$ is an amino acid residue containing a protected amino, a protected hydroxy and/or a protected carboxy, $A_e$ is an amino acid residue containing a sulfonyloxy which has a suitable substituent, $A_f$ is an amino acid residue containing an azido, $A_g$ is an amino acid residue containing an amino, $A_h$ is an amino acid residue containing a protected hydroxy, $A_i$ is an amino acid residue containing lower alkylthio, L is an acid residue, and $M_a$ and $M_b$ are each an alkaline metal.

As to the starting compounds (II) and (III), some of them are novel and can be prepared by the procedures described in the preparations and Examples mentioned later or a conventional manner.

Throughout the present specification, the amino acid, peptides, protective groups, condensing agents, etc. are indicated by the abbreviations according to the IUPAC-IUB (Commission on Biological Nomenclature) which are in common use in the field of art.

Moreover, unless otherwise indicated, the amino acids and their residues when shown by such abbreviations are meant to be L-configured compounds and residues.

Suitable pharmaceutically acceptable salts of the starting and object compound are conventional non-toxic salt and include an acid addition salt such as an organic acid salt (e.g. acetate, trifluoroacetate, maleate, tartrate, methanesulfonate, benzenesulfonate, formate, toluenesulfonate, etc.), an inorganic acid salt (e.g. hydrochloride, hydrobromide, hydriodide, sulfate, nitrate, phosphate, etc.), or a salt with an amino acid (e.g. arginine, aspartic acid, glutamic acid, etc.), or a metal salt such as an alkali metal salt (e.g. sodium salt, potassium salt, etc.) and an alkaline earth metal salt (e.g. calcium salt, magnesium salt, etc.), an ammonium salt, an organic base salt (e.g. trimethylamine salt, triethylamine salt, pyridine salt, picoline salt, dicyclohexylamine salt, N,N'-dibenzylethylenediamine salt, etc.), or the like.

In the above and subsequent descriptions of the present specification, suitable examples and illustrations of the various definitions which the present invention include within the scope thereof are explained in detail as follows.

The term "lower" is intended to mean 1 to 6, preferably 1 to 4 carbon atom(s), unless otherwise indicated.

Suitable "lower alkyl" may include a straight or branched one such as methyl, ethyl, propyl, isopropyl, butyl, isobutyl, tert-butyl, pentyl, hexyl, and the like, in which the most preferred one is methyl.

Suitable "aryl" and the aryl moiety of "arylamino" may include phenyl, tolyl, xylyl, mesityl, cumenyl, naphtyl, and the like, in which the preferred one is $C_6$-$C_{10}$ aryl and the most preferred one is phenyl.

Suitable "lower alkylene" is one having 1 to 6 carbon atom(s) and may include methylene, ethylene, trimethylene, propylene, tetramethylene, methyltrimethylene, hexamethylene, and the like, in which the preferred one is methylene, ethylene or trimethylene.

Suitable "lower alkenylene" is one having 2 to 6 carbon atom(s) and may include vinylene, propenylene, and the like, in which the preferred one is vinylene.

Suitable "an amino acid residue excepting D-Trp" means a bivalent residue derived from an amino acid excepting D-Trp, and such amino acid may be glycine (Gly), D- or L-alanine (Ala), β-alanine (βAla), D- or L-valine (Val), D- or L- leucine (Leu), D- or L-isoleucine (Ile), D- or L- serine (Ser), D- or L- threonine (Thr), D- or L-cysteine (Cys), D- or L- methionine (Met), D- or L-phenylalanine (Phe), L-tryptophan (Trp), D- or L- tyrosine (Tyr), D- or L- proline (Pro), D- or L- didehydroproline (ΔPro) such as 3,4-didehydroproline (Δ(3,4)Pro), D- or L-hydroxypropine (Pro (OH)) such as 3-hydroxyproline (Pro(3OH)) and 4- hydroxyproline (Pro(4OH)), D- or L-azetidine-2-carboxylic acid (Azt), D- or L- thioproline (Tpr), D- or L- aminoproline (Pro($NH_2$)) such as 3-aminoproline (Pro($3NH_2$)) and 4-aminoproline (Pro($4NH_2$)), D- or L- pyroglutamic acid (pGlu), D- or L-2-aminoisobutyric acid (Aib), D- or L-glutamic acid (Glu), D- or L- aspartic acid (Asp), D- or L-glutamic (Gln), D- or L- asparagine (Asn), D- or L- lysine (Lys), D- or L- arginine (Arg), D- or L-histidine (His), D- or L- ornithine (Orn), D- or L- hydroxypiperidinecarboxylic acid such as 5-hydroxypiperidine-2-carboxylic acid, D- or L- mercaptoproline (Pro(SH)) such as 3-mercaptoproline (Pro(3SH)) and 4-mercaptoproline (Pro(4SH)), whose side chains are amino, hydroxy, thiol or carboxy groups, may be substituted by the suitable substituent(s). Said suitable substituent(s) may include acyl such as carbamoyl, lower alkanoyl (e.g., formyl, acetyl, etc.), trihalo(lower) alkoxycarbonyl (e.g. 2,2,2-trichloroethoxycarbonyl, etc.), ar(lower)alkoxycarbonyl (e.g. benzyloxycarbonyl, etc.), lower alkylsulfonyl (e.g., mesyl ethylsulfonyl, etc.), lower alkoxalyl (e.g., methoxyalyl, ethoxyalyl, etc.), arylsulfonyl (e.g., phenylsulfonyl, tolylsulfonyl, etc.), haloar(lower) alkoxycarbonyl (e.g., o-chlorobenzyloxycarbonyl, etc.), carboxy(lower)alkanoyl (e.g., carboxyacetyl, carboxypropionyl, etc.), glycyl, β-alanyl, N-lower alkoxycarbonylglycyl (e.g., N-t-butoxycarbonylglycyl, etc.) and N-lower alkoxycarbonyl-β-alanyl (e.g., N-t-butoxycarbonyl-β-alanyl, etc.), N,N-di(lower)alkylamino (lower)alkanoyl (e.g., N,N-dimethylaminoacetyl, N,N-diethylaminoacetyl, N,N-dimethylaminopropionyl, N,N-diethylaminopropionyl, etc.), carboxyalyl, morpholinocarbonyl, amino(lower)alkanoyl (e.g., aminoacetyl, aminopropionyl, etc.), N-ar(lower) alkoxycarbonylamino(lower)alkanoyl (e.g. N-benzyloxycarbonylaminoacetyl, etc.), threonyl, N-lower alkoxycarbonylthreonyl (e.g. N-t-butoxycarbonylthreonyl, etc.), N-lower alkanoylthreonyl (e.g., N-acetylthreonyl, etc.), N-lower alkoxycarbonyl(lower)alkyl-N-lower alkoxycarbonylamino(lower)alkanoyl (e.g., N-t-butoxycarbonylmethyl-N-t-butoxycarbonytaminoacetyl, etc.), α-glutamyl, N-ar(lower)alkoxycarbonyl-O-ar(lower)-alkyl-αglutamyl (e.g., N-benzyloxycarbonyl-O-benzyl-α-glutamyl, etc.), γ-glutamyl, N-ar(lower)alkoxycarbonyl-O- ar(lower)alkyl-γ-glutamyl (e.g., N-benzyloxycarbonyl-O-benzyl-γ-glutamyl, etc.), lower alkyl (e.g., methyl, ethyl, t-butyl, etc.), carboxy (lower)alkyl (e.g. carboxymethyl, etc.), morpholino, glycino amide, threonino amide, N'-glutamino N-lower alkylamide (e.g., N'-glutamino N-t-butylamide, etc.), di(lower)alkylamino (e.g. dimethylamino, etc.), ar(lower)alkyl (e.g., benzyl, phenethyl, etc.), trihalo (lower)alkyl (e.g., 2,2,2-trichloroethyl, etc.), lower alkoxycarbonyl(lower)alkyl (e.g., methoxycarbonylmethyl, ethoxycarbonylmethyl, t-butoxycarbonylmethyl, etc.), or usual protecting group used in the field of art. In case that such amino acid contain a thio, it may be its sulfoxide or sulfone.

Suitable "carboxy(lower)alkyl" may include carboxymethyl, carboxyethyl, carboxypropyl, and the like.

Suitable "protected carboxy(lower)alkyl" means the above-mentioned carboxy(lower)alkyl, in which the carboxy group is protected by a conventional protective group such as esterified carboxy group. Preferred example of the ester moiety thereof may include lower alkyl ester (e.g. methyl ester, ethyl ester, propyl ester, tert-butyl ester, etc.), and the like.

Suitable "carbamoyl(lower)alkyl which may have suitable substituent(s)" may include carbamoyl(lower)alkyl (e.g., carbamoylmethyl, carbamoylethyl, carbamoylpropyl, etc.), carbamoyl(lower)alkyl having suitable substituent(s) such as lower alkylcarbamoyl(lower)alkyl (e g., methylcarbamoylmethyl, ethylcarbamoylmethyl, etc.), amino(lower)alkylcarbamoyl(lower)alkyl (e.g., aminomethylcarbamoylmethyl, aminoethylcarbamoylmethyl, etc.), lower alkylamino (lower)alkylcarbamoyl(lower)alkyl (e.g., dimethylaminomethylcarbamoylmethyl, dimethylaminoethylcarbamoylmethyl, etc.), and the like.

Suitable "lower alkyl which may have suitable substituent (s)" may include a conventional group, which is used in the field of art such as lower alkyl, carboxy(lower)alkyl, protected carboxy(lower)alkyl, carbamoyl(lower)alkyl which may have suitable substituent(s), each of which is as exemplified above, lower alkylamino(lower)alkyl (e.g. dimethylaminomethyl, dimethylaminoethyl, etc.), hydroxy (lower)alkyl (e.g., hydroxymethyl, hydroxyethyl, etc.), protected hydroxy(lower)alkyl such as acyloxy(lower)alkyl (e.g. acetyloxyethyl, etc.) halo(lower)alkyl (e.g. trifluoromethyl, etc.) and the like.

Suitable "an amino acid residue containing a thio" means a bivalent residue derived from an amino acid containing a thio, and may include Tpr, Met, and the like.

Suitable "an amino acid residue containing a sulfinyl or sulfonyl" means a bivalent residue derived from an amino acid containing a sulfinyl or sulfonyl, and may include Tpr(O), Met(O), Tpr(O²), Met(O²), and the like.

Suitable "an amino acid residue containing an amino, a hydroxy and/or a carboxy" may include a bivalent residue of an amino acid such as Pro(4OH), Ser, Thr, Tyr, and the like.

Suitable "an amino acid residue containing a protected amino, a protected hydroxy and/or a protected carboxy" means the above-mentioned group, in which the amino, hydroxy and/or carboxy is protected by a conventional group used in the field of the art such as carbamoyl, lower alkylsulfonyl (e.g., mesyl, ethylsulfonyl, etc.), arylsulfonyl (e.g., phenylsulfonyl, tolylsulfonyl, etc.), lower alkoxycarbonyl(lower)alkyl (e.g., methoxycarbonylmethyl, ethoxycarbonylmethyl, etc.), and the like.

Suitable "an amino acid residue containing sulfonyloxy which has a suitable substituent" means a bivalent residue derived from an amine acid containing sulfonyloxy which has a suitable substituent, in which "sulfonyloxy which has a suitable substituent" may include lower alkylsulfonyloxy (e.g., methylsulfonyloxy, ethylsulfonyloxy, etc.), halo (lower)alkylsulfonyloxy (e.g., trifluoromethylsulfonyloxy, etc.), arylsulfonyloxy (e.g., phenylsulfonyloxy, tolylsulfonyloxy, etc.), and the like.

Suitable "an amino acid residue containing an azido" may include a bivalent residue of an amino acid such as Pro (4N₃), and the like.

Suitable "an amino acid residue containing an amino" may include a bivalent residue of an amino acid such as Pro(4NH₂), and the like.

Suitable "an amino acid residue containing a protected hydroxy" means the above-mentioned group, in which the hydroxy is protected by a conventional group as mentioned above.

Suitable "alkaline metal" may include sodium, potassium, and the like.

Suitable "an acid residue" may include halogen (e.g., fluoro, chloro, bromo, iodo), acyloxy (e.g., tosyloxy, mesyloxy, etc.), and the like.

Suitable "ar(lower)alkyl which may have suitable substituent(s)" may include a conventional group, which is used in the field of amino acid and peptide chemistry, such as ar(lower)alkyl (e.g. trityl, benzhydryl, benzyl, phenethyl, etc.), substituted ar(lower)alkyl (e.g., o-fluorobenzyl, m-fluorobenzyl, o-trifluoromethylbenzyl, etc.), and the like.

Suitable "pyridyl(lower)alkyl" may include 2-pyridylmethyl, 3-pyridylmethyl, 4-pyridylmethyl, and the like.

Suitable group of the formula:

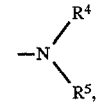

in which $R^4$ and $R^5$ are linked together to form benzene-condensed lower alkylene, may include 1-indolinyl, 2-isoindolinyl, 1,2,3,4-tetrahydroquinolin-1-yl, 1,2,3,4-tetrahydroisoquinolin-2-yl, and the like.

Suitable "hydroxy(lower)alkyl" may include hydroxymethyl, hydroxyethyl, hydroxypropyl, and the like.

Suitable "protected hydroxy(lower)alkyl" means the above-mentioned hydroxy(lower)alkyl, in which the hydroxy group is protected by a conventional protective group such as acyl (e.g. acetyl, etc.), and may include acetyloxyethyl and the like.

Suitable "amino protective group" may be a conventional protective group, which is used in the field of amino acid and peptide chemistry, that is, may include acyl such as lower alkanoyl (e.g. formyl, acetyl, propionyl, butyryl, isobutyryl, valeryl, isovaleryl, pivaloyl, hexanoyl, etc.), lower alkoxycarbonyl (e.g. methoxycarbonyl, ethoxycarbonyl, propoxycarbonyl, butoxycarbonyl, t-butoxycarbonyl, etc.), lower alkanesulfonyl (e.g. methanesulfonyl, ethanesulfonyl, etc.), and the like.

Suitable "an amino acid residue containing lower alkylthio" means a bivalent residue of an amino acid containing lower alkylthio, in which lower alkylthio may include methylthio, ethylthio, and the like.

Suitable "carboxy(lower)alkoxy" may include carboxymethoxy, carboxyethoxy, carboxypropoxy, and the like.

Suitable "protected carboxy(lower)alkoxy" means the above-mentioned carboxy(lower)alkoxy, in which the carboxy group is protected by a conventional protective group such as esterified carboxy group. Preferred example of the ester moiety thereof may include lower alkyl ester (e.g. methyl ester, ethyl ester, propyl ester, tert-butyl ester, etc.), and the like.

Suitable substituent on $R^1$ moiety may include a conventional group, which is used in the field of amino acid and peptide chemistry, such as lower alkyl which may have suitable substituent(s), amino protective group, each as defined above, hydroxy, halogen (e.g. fluoro, chloro, etc.), lower alkoxy (e.g. methoxy, butoxy, etc.), N,N-di(lower)alkylamino (e.g. dimethylamino, etc.), lower alkoxycarbonyl (e.g. methoxycarbonyl, t-butoxycarbonyl, etc.), and the like.

Suitable substituent for $R^3$ and $R^7$ may include a conventional group, which is used in the field of amino acid and peptide chemistry, such as lower alkyl which may have suitable substituent(s) as mentioned above, carboxy(lower)alkoxy, protected carboxy(lower)alkoxy, each as defined above, halogen (e.g. fluoro, chloro, etc.), lower alkoxy (e.g. methoxy, butoxy, etc.), nitro, amino, protected amino, in which amino protective group is as defined above, and the like.

Particularly, the preferred embodiments of $R^1$, $R^2$, $R^3$, $R^4$, $R^5$, $R^7$, A and Y are as follows $R^1$ is aryl such as phenyl and naphthyl, which may have one or more, preferably one to three halogen or lower alkoxy (e.g. phenyl, difluorophenyl, dimethoxyphenyl, etc.);

benzofuryl;

pyridyl;

or a group of the formula:

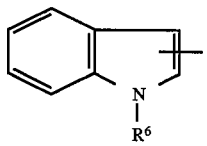

wherein $R^6$ is hydrogen;
lower alkyl (e.g. methyl, etc.); or
N,N-di(lower)alkylamino(lower)alkyl (e.g. dimethylaminoethyl, etc.);

$R^2$ is hydrogen; or
lower alkyl (e.g. methyl, etc.);

$R^3$ is lower alkyl which may have one or more, preferably one to three halogen (e.g. methyl, trifluoromethyl, etc.);
amino;
acylamino such as lower alkanesulfonylamino (e.g. methanesulfonylamino, etc.);
carboxy(lower)alkoxy (e.g. carboxymethoxy, etc.);
esterified carboxy(lower)alkyl such as lower alkoxycarbonyl(lower)alkoxy (e.g. ethoxycarbonylmethoxy, etc.);
halogen (e.g. fluoro, chloro, etc.);
lower alkoxy (e.g. methoxy, etc.); or
nitro;

$R^4$ is lower alkyl (e.g. methyl, etc.);

$R^5$ is ar(lower)alkyl such as mono or di or triphenyl (lower)alkyl, preferably phenyl(lower)alkyl (e.g. benzyl, etc.);

$R^7$ is hydrogen;
lower alkyl (e.g. methyl, etc.); or
halogen (e.g. chloro, etc.);

A is a bivalent residue derived from an am(no acid excepting D-Trp, which may have suitable substituent (s) such as hydroxyproline (e.g. 4-hydroxyproline, etc.); or didehydroproline (e.g. 3,4-didehydroproline, etc.); and Y is bond;
lower alkylene (e.g. ethylene, etc.); or
lower alkenylene (e.g. vinylene, etc.).

Also, the preferred embodiments of $R^1$, $R^2$, $R^3$, $R^4$, $R^5$, $R^7$, A and Y are as follows.

$R^1$ is aryl which may have one or more, preferably one to three halogen (e.g. phenyl, difluorophenyl, etc.); benzofulyl;
or a group of the formula:

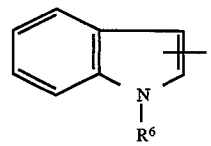

wherein $R^6$ is hydrogen;
lower alkyl (e.g. methyl, etc.); or
N,N-di(lower)alkylamino(lower)alkyl (e.g. dimethylaminoethyl, etc.);

$R^2$ is hydrogen; or
lower alkyl (e.g. methyl, etc.);

$R^3$ is lower alkyl which may have halogen (e.g. methyl, trifluoromethyl, etc.);
amino;
lower alkanesulfonylamino (e.g. methanesulfonylamino, etc.);
carboxy(lower)alkoxy (e.g. carboxymethoxy, etc.);
lower alkoxycarbonyl(lower)alkoxy (e.g. ethoxycarbonylmethoxy, etc.);
halogen (e.g. fluoro, etc.);
lower alkoxy (e.g. methoxy, etc.); or nitro;

$R^4$ is lower alkyl (e.g. methyl, etc.);

$R^5$ is ar(lower)alkyl such as mono or di or triphenyl (lower)alkyl, (e.g. benzyl, etc.);

$R^7$ is hydrogen;
lower alkyl (e.g. methyl, etc.); or
halogen (e.g. chloro, etc.);

A is a bivalent residue derived from an amino acid excepting D-Trp, which may have suitable substituent (s) such as hydroxyproline (e.g. 4-hydroxyproline, etc.), didehydroproline (e.g. 3,4-didehydroproline, etc.); and Y is bond;
lower alkenylene (e.g. vinylene, etc.).

The processes for preparing the object compound (I) are explained in detail in the following.

PROCESS 1

The object compound (I) or a salt thereof can be prepared by reacting the compound (II) or its reactive derivative at the amino group or a salt thereof with the compound (III) or its reactive derivative at the carboxy group or a salt thereof.

Suitable reactive derivative at the amino group of the compound (II) may include Schiff's base type imino or its tautomeric enamine type isomer formed by the reaction of the compound (II) with a carbonyl compound such as aldehyde, ketone or the like; a silyl derivative formed by the reaction of the compound (II) with a silyl compound such as bis(trimethylsilyl)acetamide, mono(trimethylsyliy) acetamide, bis(trimethylsilyl)urea or the like; a derivative formed by reaction of the compound (II) with phosphorus trichloride or phosgene, and the like.

Suitable salts of the compound (II) and its reactive derivative can be referred to the ones as exemplified for the compound (I).

Suitable reactive derivative at the carboxy group of the compound (III) may include an acid halide, an acid anhydride, an activated amide, an activated ester, and the like. Suitable examples of the reactive derivatives may be an acid chloride; an acid azide; a mixed acid anhydride within acid such as substituted phosphoric acid [e.g. dialkylphosphoric acid, phenylphosphoric acid, diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivalic acid, pentanoic acid, isopentanoic acid, 2-ethylbutyric acid, trichloroacetic acid, etc.] or aromatic carboxylic acid [e.g. benzoic acid, etc.]; a symmetrical acid anhydride; an activated amide with imidazole, 4-substituted imidazole, dimethylpyrazole, triazole or tetrazole; or an activated ester [e.g. cyanomethyl ester, methoxymethyl ester, dimethyliminomethyl [/CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound (III) to be used.

Suitable salts of the compound (III) and its reactive derivative may be a base salt such as an alkali metal salt [e.g. sodium salt, potassium salt, etc.], an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N'-dibenzylethylenediamine salt, etc.], or the like, and an acid addition salt as exemplified for the compound (I).

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound (III) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide; N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; diphenyl phosphorylazide; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; benzotriazol-1-yl-oxy-tris-(dimethylamino) phosphoniumhexafluorophosphate; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, etc.; or the like.

The reaction may also be carried out in the presence of an inorganic or organic base such as an alkali metal bicarbonate, tri(lower)alkylamine, pyridine, N-(lower)alkylmorpholine, N,N-di(lower)alkylbenzylamine, or the like.

The reaction temperature is not critical, and the reaction is usually carried out under cooling to warming.

PROCESS 2

The object compound (I-b) or a salt thereof can be prepared by reacting the compound (I-a) or a salt thereof with the compound (IV).

The present reaction is usually carried out in the presence of a base such as alkyl lithium (e.g. n-butyl lithium, etc.), alkali metal hydride (e.g. sodium hydride, potassium hydride, etc.), tri(lower)alkylamine (e.g. trimethylamine, triethylamine, etc.), pyridine or its derivative (e.g. picoline, lutidine, 4-dimethylaminopyridine, etc.), or the like.

The present reaction is usually carried out in a solvent such as dioxane, dimethyl sulfoxide, dimethylformamide, diethylformamide, dimethylacetamide, benzene, tetrahydrofuran, or any other solvent which does not adversely affect the reaction. In case that the base to be used is liquid, it can also be used as a solvent.

If necessary, the present reaction can be used phase transfer catalyst (e.g. cetyltrimethylammonium chloride, etc.).

The reaction temperature is not critical and the reaction is usually carried out under cooling, at ambient temperature or under heating.

The present reaction includes, within its scope, the case that the hydroxy group on A is reacted during the reaction or at the post-treating step of the present process.

PROCESS 3

The object compound (I-d) or a salt thereof can be prepared by subjecting the compound (I-c) or a salt thereof to elimination reaction of the carboxy protective group.

In the present elimination reaction, all conventional methods used in the elimination reaction of the carboxy protective group, for example, hydrolysis, reduction, elimination using Lewis acid, etc. are applicable. When the carboxy protective group is an ester, it can be eliminated by hydrolysis or elimination using Lewis acid. The hydrolysis is preferably carried out in the presence of a base or an acid.

Suitable base may include, for example, an inorganic base such as alkali metal hydroxide (e.g. sodium hydroxide, potassium hydroxide, etc.), alkaline earth metal hydroxide (e.g. magnesium hydroxide, calcium hydroxide, etc.), alkali metal carbonate (e.g. sodium carbonate, potassium carbonate, etc.), alkaline earth metal carbonate (e.g. magnesium carbonate, calcium carbonate, etc.), alkali metal bicarbonate (e.g. sodium bicarbonate, potassium bicarbonate, etc.), alkali metal acetate (e.g. sodium acetate, potassium acetate, etc.), alkaline earth metal phosphate (e.g. magnesium phosphate, calcium phosphate, etc.), alkali metal hydrogen phosphate (e.g. disodium hydrogen phosphate, dipotassium hydrogen phosphate, etc.), or the like, and an organic base such as trialkylamine (e.g. trimethylamine, triethylamine, etc.), picoline, N-methylpyrrolidine, N-methylmorpholine, 1,5-diazabicyclo[4.3.0]non-5-one, 1,4-diazabicyclo[2.2.2]octane, 1,5-diazabicyclo[5.4.0]undecene-5 or the like. The hydrolysis using a base is often carried out in water or a hydrophilic organic solvent or a mixed solvent thereof.

Suitable acid may include an organic acid (e.g. formic acid, acetic acid, propionic acid, etc.) and an inorganic acid (e.g. hydrochloric acid, hydrobromic acid, sulfuric acid, etc.).

The present hydrolysis is usually carried out in an organic solvent, water, or a mixed solvent thereof.

The reaction temperature is not critical, and it may suitably be selected in accordance with the kind of the carboxyprotective group and the elimination method.

The elimination using Lewis acid is carried out by reacting the compound (I-c) or a salt thereof with Lewis acid such as boron trihalide (e.g. boron trichloride, boron trifluoride, etc.), titanium tetrahalide (e.g. titanium tetrachloride, titanium tetrabromide, etc.), tin tetrahalide (e.g. tin tetrachloride, tin tetrabromide, etc.), aluminum halide (e.g. aluminum chloride, aluminum bromide, etc.), trihaloacetic acid (e.g. trichloroacetic acid, trifluoroacetic acid, etc.) or the like. This elimination reaction is preferably carried out in the presence of cation trapping agents (e.g. anisole, phenol, etc.) and is usually carried out in a solvent such as nitroalkane (e.g. nitromethane, nitroethane, etc.), alkylene halide (e.g. methylene chloride, ethylene chloride, etc.), diethyl ether, carbon disulfide or any other solvent which does not adversely affect the reaction. These solvents may be used as a mixture thereof.

The reduction elimination can be applied preferably for elimination of the protective group such as halo(lower)alkyl (e.g. 2-iodoethyl, 2,2,2-trichloroethyl, etc.) ester, ar(lower)alkyl (e.g. benzyl, etc.) ester or the like.

The reduction method applicable for the elimination reacting may include, for example, reduction by using a combination of a metal (e.g. zinc, zinc amalgam, etc.) or a salt of chromium compound (e.g. chromous chloride, chromous acetate, etc.) and an organic or an inorganic acid (e.g. acetic acid, propionic acid, hydrochloric acid, etc.); and conventional catalytic reduction in the presence of a conventional metallic catalyst (e.g. palladium carbon, Raney nickel, etc.).

The reaction temperature is not critical, and the reaction is usually carried out under cooling, at ambient temperature or under warming.

The present elimination reaction includes, within its scope, the case that the amino, hydroxy and/or carboxy protective group for A is eliminated during the reaction or at the post-treating step of the present process.

PROCESS 4

The object compound (I-e) or a salt thereof can be prepared by subjecting the compound (I-d) or its reactive derivative at the carboxy group or a salt thereof to amidation.

The amidating agent to be used in the present amidation may include amine which may have suitable substituent(s) such as lower alkyl (e.g., methyl, ethyl, etc.), amino(lower)alkyl (e.g., aminomethyl, aminoethyl, etc.), lower alkylamino(lower)alkyl (e.g., dimethylaminomethyl, dimethylaminoethyl, etc.) and the like.

Suitable reactive derivative at the carboxy group of the compound (I-d) can be referred to the ones as exemplified for the compound (III) in Process 1.

This reaction can be carried out in substantially the same manner as Process 1, and therefore the reaction mode and reaction conditions [e.g. reaction derivatives, solvents, reaction temperature, etc.] of this reaction are to be referred to those as explained in Process 1.

PROCESS 5

The object compound (I-g) or a salt thereof can be prepared by oxidizing the compound (I-f) or a salt thereof.

The oxidizing agent to be used in this reaction may include an inorganic peracid or a salt thereof (e.g. periodic acid, persulfuric acid, or sodium or potassium salt thereof, etc.), an organic peracid or a salt thereof (e.g. perbenzoic acid, m-chloroperbenzoic acid, performic acid, peracetic acid, chloroperacetic acid, trifluoroperacetic acid, or sodium or potassium salt, thereof, etc.), ozone, hydrogen peroxide, urea-hydrogen peroxide, N-halosuccinimide (e.g. N-bromosuccinimide, N-chlorosuccinimide, etc.), hydrochlorite compound (e.g. tert-butyl hydrochlorite, etc.) permanganate (e.g. potassium permanganate, etc.), or any other conventional oxidizing agent which can oxidide a sulfinyl group to a sulfonyl group.

The present reaction can also be carried out in the presence of a compound comprising Group Vb or VIb metal in the Periodic Table of elements, for example, tungstic acid, molybdic acid, vanadic acid, etc., or an alkali or an alkaline earth metal salt thereof.

The present oxidation reaction is usually carried out in a conventional solvent which does not adversely influence the reaction such as water, acetic acid, chloroform, methylene chloride, acetone, methanol, ethanol or a mixture thereof.

The reaction temperature is not critical and the reaction is preferably carried out under cooling to at ambient temperature.

PROCESS 6

The object compound (I-i) or a salt thereof can be prepared by subjecting the compound (I-h) or its reactive derivative at the amino, hydroxy and/or carboxy group or a salt thereof to introduction reaction of the amino, hydroxy and/or carboxy protective group.

The reaction can be carried out in substantially the same manner as Process 1, and therefore the reaction mode and reaction conditions [e.g. solvents, reaction temperature, etc.] of this reaction are to be referred to those as explained in Process 1.

The present reaction includes, within its scope, the case that the amino group on $R^1$ is reacted during the reaction or at the post-treating step of the present process.

PROCESS 7-(i)

The compound (VI) or a salt thereof can be prepared by reacting the compound (I-j) or a salt thereof with the compound (V).

The reaction is usually carried out in a conventional solvent such as dimethyl sulfoxide or any other solvent which does not adversely influence the reaction.

The reaction temperature is not critical and the reaction is usually carried out under warming to heating.

PROCESS 7-(ii)

The object compound (I-k) or a salt thereof can be prepared by subjecting the compound (VI) or a salt thereof to hydrogenation. This reaction is usually carried out in the presence of triphenylphosphine, palladium on carbon, or the like.

The reaction is usually carried out in a conventional solvent such as alcohol (e.g., methanol, ethanol, etc.), or any other solvent which does not adversely influence the reaction.

The reaction temperature is not critical and the reaction is usually carried out under cooling to heating.

PROCESS 8

The object compound (I-h) or a salt thereof can be prepared by subjecting the compound (I-i) or a salt thereof to elimination reaction of the amino, hydroxy and/or carboxy protective group.

This reaction can be carried out in substantially the same manner at Process 3, and therefore the reaction mode and reaction conditions [e.g. bases, acids, reducing agents, catalysts, solvents, reaction temperature, etc.] of this reaction are to be referred to those as explained in Process 3.

The present elimination reaction includes, within its scope, the case that the carboxy protective group for $R^1$ is eliminated during the reaction or at the post-treating step of the present process.

PROCESS 9

The object compound (I-l) or a salt thereof can be prepared by reacting the compound (I-k) or a salt thereof with the compound (VI).

The reaction is usually carried out in a conventional solvent such as N,N-dimethylformamide or any other solvent which does not adversely influence the reaction.

The reaction temperature is not critical and the reaction is usually carried out under cooling to heating.

PROCESS 10

The object compound (I-a) or a salt thereof can be prepared by subjecting the compound (I-m) or a salt thereof to elimination reaction of the amino, protective group.

This reaction can be carried out in substantially the same manner as Process 3, and therefore the reaction mode and reaction conditions [e.g. bases, acids, reducing agents, catalysts, solvents, reaction temperature, etc.] of this reaction are to be referred to those as explained in Process 3.

PROCESS 11

The object compound (I-o) or a salt thereof can be prepared by subjecting the compound (I-n) or a salt thereof to elimination reaction of the hydroxy protective group.

This reaction can be carried out in substantially the same manner as Process 3, and therefore the reaction mode and reaction conditions [e.g. bases, acids, reducing agents, catalysts, solvents, reaction temperature, etc.] of this reaction are to be referred to those as explained in Process 3.

PROCESS 12

The object compound (I-q) or a salt thereof can be prepared by subjecting the compound (I-p) or a salt thereof to elimination reaction of the carboxy, protective group.

This reaction can be carried out in substantially the same manner as Process 3, and therefore the reaction mode and reaction conditions [e.g. bases, acids, reducing agents, catalysts, solvents, reaction temperature, etc.] of this reaction are to be referred to those as explained in Process 3.

PROCESS 13

The object compound (I-s) or a salt thereof can be prepared by subjecting the compound (I-r) or a salt thereof to reduction.

This reaction can be carried out in substantially the same manner as Process 3, and therefore the reaction mode and reaction conditions [e.g. bases, acids, reducing agents, catalysts, solvents, reaction temperature, etc.] of this reaction are to be referred to those as explained in Process 3.

The compounds obtained by the above processes can be isolated and purified by a conventional method such as pulverization, recrystallization, column chromatography, reprecipitation, or the like.

It is to be noted that the compound (I) and the other compounds may include one or more stereoisomers due to asymmetric carbon atoms, and all of such isomers and mixture thereof are included within the scope of this invention.

The object compounds (I) and pharmaceutically acceptable salt thereof have pharmacological activities such as tachykinin antagonism, especially substance P antagonism, neurokinin A antagonism or neurokinin B antagonism, and therefore are useful for treating or preventing tachykinin mediated diseases, for example, respiratory diseases such as asthma, bronchitis, rhinitis, cough, expectoration, and the like; ophthalmic diseases such as conjunctivitis, vernal conjunctivitis, and the like; cutaneous diseases such as contact dermatitis, atopic dermatitis, urticaria, and other eczematoid dermatitis, and the like; inflammatory diseases such as rheumatoid arthritis, osteoarthritis, and the like; pains or aches (e.g. migraine, headache, toothache, cancerous pain, back pain, etc.); and the like.

Further, it is expected that the object compounds (I) of the present invention are useful for treating or preventing ophthalmic diseases such as glaucoma, uveitis, and the like; gastrointestinal diseases such as ulcer, ulcerative colitis, irritable bowel syndrome, food allergy, and the like; inflammatory diseases such as nephritis, and the like; circulatory diseases such as hypertension, angina pectoris, cardiac failure, thrombosis, and the like; epilepsy; spartic paralysis; pollakiuria; dementia; Alzheimer's diseases; schizophrenia; Huntington's chorea; carcinoid syndrome; and the like, and useful for immunosuppresive agent.

For therapeutic purpose, the compounds (I) and pharmaceutically acceptable salts thereof of the present invention can be used in a form of pharmaceutical preparation containing one of said compounds, as an active ingredient, in admixture with a pharmaceutically acceptable carrier such as an organic or inorganic solid or liquid excipient suitable for oral, parenteral or external administration. The pharmaceutical preparations may be capsules, tablets, dragees, granules, solution, suspension, emulsion, or the like. If desired, there may be included in these preparation, auxiliary substances, stabilizing agents, wetting or emulsifying agents, buffers and other commonly used additives.

While the dosage of the compounds (I) will vary depending upon the age and condition of the patient, an average single dose of about 0.1 mg, 1 mg, 10 mg, 50 mg, 100 mg, 250 mg, 500 mg and 1000 mg of the compound (I) may be effective for treating asthma and the like. In general, amounts between 0.1 mg/body and about 1,000 mg/body may be administered per day.

In order to illustrate the usefulness of the object compound (I), the pharmacological test data of some representative compound of the compound (I) is shown in the following.

Test Compound

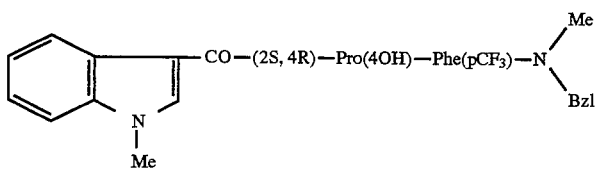

(1) ³H-Substance P receptor binding

Test Method (a) Crude lung membrane preparation

Male Hartly strain guinea pigs were sacrificed by decapitation. The trachea and lung were removed and homogenized in buffer (0.25M sucrose, 50 mM Tris-HCl pH 7.5, 0.1 mM EDTA) by suing Polytoron (Kinematica). The homogenate was centrifuged (1000 xg, 10 min) to remove tissue clumps and the supernatant was centrifuges (14000 xg 20 min) to yield pellets. The pellets were resuspended in buffer (5 mM Tris-HCl pH 7.5), homogenized with a teflon homogenizer and centrifuged (14000 xg, 20 min) to yield pellets which were referred to as crude membrane fractions. The obtained pallets were stored at −70° C. until use.

(b) ³H-Substance P binding to preparation membrane

Frozen crude membrane fractions were thawed and resuspended in Medium 1 (50 mM Tris-HCl pH 7.5, 5 mM MnCl₂, 0.02% BSA, 2 µg/ml chymostatin, 4 µg/ml leupeptin, 40 µg/ml bacitracin.) ³H-substance P (1 nM) was incubated with 100 µl of the membrane preparation in Medium 1 at 4° C. for 30 minutes in a final volume of 500 µl. At the end of the incubation period, reaction mixture was quickly filtered over a Whatman GF/B glass filter (pretreated with 0.1% polyethylene imine for 3 hours prior to use) under aspiration. The filters were then washed four times with 5 ml of the buffer (50 mM Tris-HCl, pH 7.5). The radioactivity was counted in 5 ml of Aquazol-2 in Packerd scintillation counter (Packerd TRI -CARB 4530).

Test Result

| Test Compound (0.1 µg/ml) | Inhibition (%) |
|---|---|
| (a) | 96 |

The following examples are given for purpose of illustrating the present invention in detail.

In these examples, there are employed the following abbreviations in addition to the abbreviations adopted by the IUPAC-IUB.

Ac: acetyl
Aib: 2-aminoisobutyric acid
Azt: azetidine-2-carboxylic acid
Boc: t-butoxycarbonyl
BSA: bistrimethylsilylacetamide
Bu$^t$: t-butyl
Bz: benzoyl
Bzl: benzyl
Bzl(o-F): o-fluorobenzyl
Bzl(m-F): m-fluorobenzyl (a)

Bzl(o-CF₃): o-trifluoromethylbenzyl
DMAP: dimethylaminopyridine
DMF: dimethylformamide
DMSO: dimethylsulfoxide
Et: ethyl
HOBT: N-hydroxybenzotriazole
IPE: isopropyl ether
Me: methyl
Ms: mesyl
NMM: N-methylmorpholine
HCl/DOX: hydrogen chloride in 1,4-dioxane
Pr$^i$: isopropyl
Py(2): 2-pyridyl
Su: succinimido
TEA: triethylamine
TFA: trifluoroacetic acid
THF: tetrahydrofuran
Tpr: thioproline
Ts: tosyl
WSC: 1-ethyl-3-(3'-dimethylaminopropyl)carbodiimide
Z: benzyloxycarbonyl The Starting Compounds used and the Object Compounds obtained in the following examples are given in The Table as below, in which the formulae of the former compounds are in the upper and the formulae of the latter compounds are in the lower, respectively.

TABLE
| Preparation No. | Formula |
|---|---|
| 1 | H—Phe(p-CF$_3$)—OH |
|   | Boc—Phe(p-CH$_3$)—OH |
| 2-(1) | H—Phe(p-F)—OH |
|   | Boc—Phe(p-F)—OH |
| 2-(2) | H—Phe(o-F)—OH |
|   | Boc—Phe(o-F)—OH |
| 2-(3) | H—Phe(m-F)—OH |
|   | Boc—Phe(m-F)—OH |
| 2-(4) | H—Phe(m-CF$_3$)—OH |
|   | Boc—Phe(m-CF$_3$)—OH |
| 3 | Boc—Phe(p-CF$_3$)—OH |
|   | 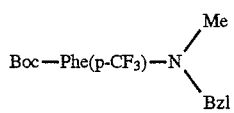 |
| 4-(1) | Boc—Phe(p-NO$_2$)—OH |
|   | 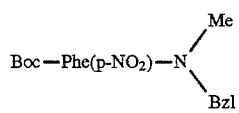 |
| 4-(2) | Boc—Phe(o-F)—OH |
|   | 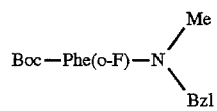 |
| 4-(3) | Boc—Phe(p-F)—OH |
|   | 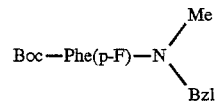 |
| 4-(4) | Boc—Phe(m-F)—OH |
|   | 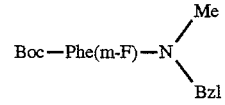 |
| 4-(5) | Boc—Phe(m-CF$_3$)—OH |
|   | 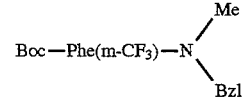 |
| 4-(6) | Boc—Phe(p-OH)—OH |
|   | 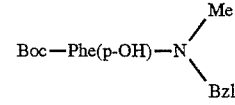 |
| 5 | 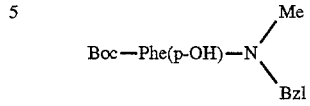 |
|   | 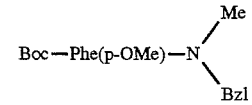 |

TABLE-continued

| | |
|---|---|
| 6 | Boc—Phe(p-CF₃)—N(Me)(Bzl) |
| | HCl·H—Phe(p-CF₃)—N(Me)(Bzl) |
| 7-(1) | Boc—Phe(p-NO₂)—N(Me)(Bzl) |
| | HCl·H—Phe(p-NO₂)—N(Me)(Bzl) |
| 7-(2) | Boc—Phe(p-NHMs)—N(Me)(Bzl) |
| | HCl·H—Phe(p-NHMs)—N(Me)(Bzl) |
| 7-(3) | Boc—Phe(m-F)—N(Me)(Bzl) |
| | HCl·H—Phe(m-F)—N(Me)(Bzl) |
| 7-(4) | Boc—Phe(m-CF₃)—N(Me)(Bzl) |
| | HCl·H—Phe(m-CF₃)—N(Me)(Bzl) |
| 7-(5) | Boc—Phe(p-OMe)—N(Me)(Bzl) |
| | HCl·H—Phe(p-OMe)—N(Me)(Bzl) |
| 8 | HCl·H—Phe(p-CF₃)—N(Me)(Bzl) |
| | Boc-(2S,4R)-Pro(4OH)—Phe(p-CF₃)—N(Me)(Bzl) |

TABLE-continued

| | |
|---|---|
| 9-(1) | HCl.—Phe(p-CF₃)—N(Me)(Bzl) |
| | Boc-Δ(3,4)Pro—Phe(p-CF₃)—N(Me)(Bzl) |
| 9-(2) | HCl.H—Phe(p-NO₂)—N(Me)(Bzl) |
| | Boc-(2S,4R)-Pro(4OH)—Phe(p-NO₂)—N(Me)(Bzl) |
| 9-(3) | HCl.H—Phe(p-NHMs)—N(Me)(Bzl) |
| | Boc-(2S,4R)-Pro(4OH)—Phe(p-NHMs)—N(Me)(Bzl) |
| 9-(4) | HCl.H—Phe(m-F)—N(Me)(Bzl) |
| | Boc-(2S,4R)-Pro(4OH)—Phe(m-F)—N(Me)(Bzl) |
| 9-(5) | HCl.H—Phe(m-CF₃)—N(Me)(Bzl) |
| | Boc-(2S,4R)-Pro(4OH)—Phe(m-CF₃)—N(Me)(Bzl) |
| 9-(6) | HCl.H—Phe(p-OMe)—N(Me)(Bzl) |
| | Boc-(2S,4R)-Pro(4OH)—Phe(p-OMe)—N(Me)(Mzl) |
| 10 | Boc—Phe(p-NO₂)—N(Me)(Bzl) |
| | Boc—Phe(p-NH₂)—N(Me)(Bzl) |

TABLE-continued
11 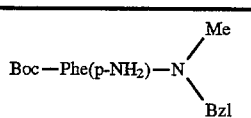
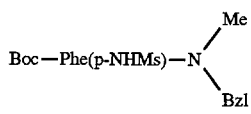
12-(1) 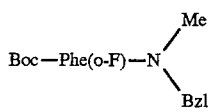
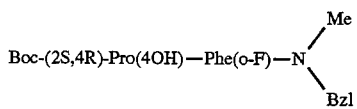
12-(2) 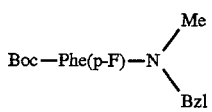
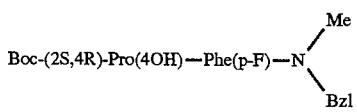
12-(3) 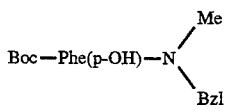
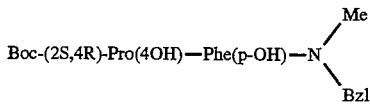
13 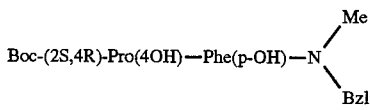
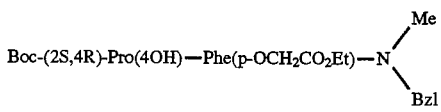
14 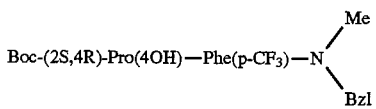
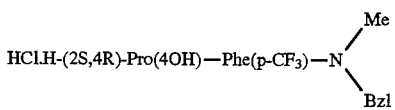
15-(1) 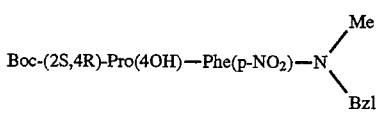
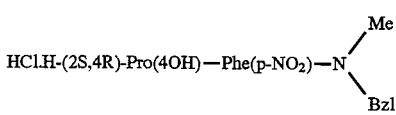

TABLE-continued 15-(2)
Boc-(2S,4R)-Pro-(4OH)—Phe(p-NHMs)—N(Me)(Bzl)

HCl.H-(2S,4R)-Pro(4OH)—Phe(p-NHMs)—N(Me)(Bzl)

15-(3)
Boc-(2S,4R)-Pro(4OH)—Phe(o-F)—N(Me)(Bzl)

HCl.H-(2S,4R)-Pro(4OH)—Phe(o-F)—N(Me)(Bzl)

15-(4)
Boc-(2S,4R)-Pro(4OH)—Phe(p-F)—N(Me)(Bzl)

HCl.H-(2S,4R)-Pro(4OH)—Phe(p-F)—N(Me)(Bzl)

15-(5)
Boc-(2S,4R)-Pro(4OH)—Phe(m-F)—N(Me)(Bzl)

HCl.H-(2S,4R)-Pro(4OH)—Phe(m-F)—N(Me)(Bzl)

15-(6)
Boc-(2S,4R)-Pro(4OH)—Phe(p-OCH$_2$CO$_2$Et)—N(Me)(Bzl)

HCl.H-(2S,4R)-Pro(4OH)—Phe(p-OCH$_2$CO$_2$Et)—N(Me)(Bzl)

15-(7)
Boc-(2S,4R)-Pro(4OH)—Phe(m-CF$_3$)—N(Me)(Bzl)

HCl.H-(2S,4R)-Pro(4OH)—Phe(m-CF$_3$)—N(Me)(Bzl)

15-(8)
Boc-(2S,4R)-Pro(4OH)—Phe(p-OMe)—N(Me)(Bzl)

HCl.H(2S,4R)-Pro(4OH)—Phe(p-OMe)—N(Me)(Bzl)

TABLE-continued

| | |
|---|---|
| 16 | H—Phe(3,4-diMe)—OH |
| | Boc—Phe(3,4-diMe)—OH |
| 17 | Boc—Phe(3,4-diMe)—OH |
| | Boc—Phe(3,4-diMe)—N(Me)(Bzl) |
| 18 | Boc—Phe(3,4-diMe)—N(Me)(Bzl) |
| | HCl.H—Phe(3,4-diMe)—N(Me)(Bzl) |
| 19 | HCl.H—Phe(3,4-diMe)—N(Me)(Bzl) |
| | Boc-(2S,4R)-Pro(4OH)—Phe(3,4-diMe)—N(Me)(Bzl) |
| 20 | Boc-(2S,4R)-Pro(4OH)—Phe(3,4-diMe)—N(Me)(Bzl) |
| | TFA.H-(2S,4R)-Pro(4OH)—Phe(3,4-diMe)—N(Me)(Bzl) |
| 21 | Ac—Phe(3,4-diCl)—OH |
| | H—Phe(3,4-diCl)—OH |
| 22 | Boc—Phe(3,4-diMe)—OH |
| | Boc—MePhe(3,4-diMe)—OH |
| 23 | H—Phe(3,4-diCl)—OH |
| | Boc—Phe(3,4-diCl)—OH |
| 24 | Boc—Phe(3,4-diCl)—OH |
| | Boc—Phe(3,4-diCl)—N(Me)(Bzl) |
| 25 | Boc—MePhe(3,4-diMe)—OH |
| | Boc—MePhe(3,4-diMe)—N(Me)(Bzl) |
| 26 | Boc—Phe(3,4-diCl)—N(Me)(Bzl) |
| | Boc-(2S,4R)-Pro(4OH)—Phe(3,4-diCl)—N(Me)(Bzl) |

TABLE-continued

| | |
|---|---|
| 27 | 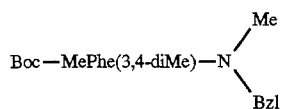 Boc—MePhe(3,4-diMe)—N(Me)(Bzl) |
| | 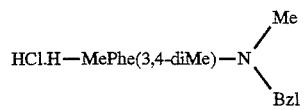 HCl.H—MePhe(3,4-diMe)—N(Me)(Bzl) |
| 28 | 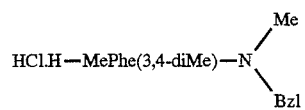 HCl.H—MePhe(3,4-diMe)—N(Me)(Bzl) |
| | 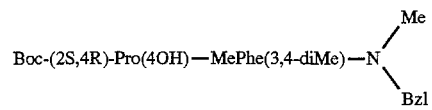 Boc-(2S,4R)-Pro(4OH)—MePhe(3,4-diMe)—N(Me)(Bzl) |
| 29 | 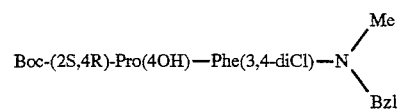 Boc-(2S,4R)-Pro(4OH)—Phe(3,4-diCl)—N(Me)(Bzl) |
| | 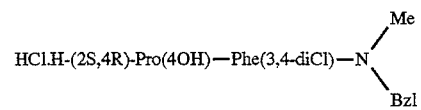 HCl.H-(2S,4R)-Pro(4OH)—Phe(3,4-diCl)—N(Me)(Bzl) |

| Example No. | Formula |
|---|---|
| 1 | 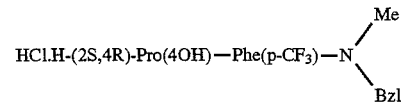 HCl.H-(2S,4R)-Pro(4OH)—Phe(p-CF$_3$)—N(Me)(Bzl) |
| | 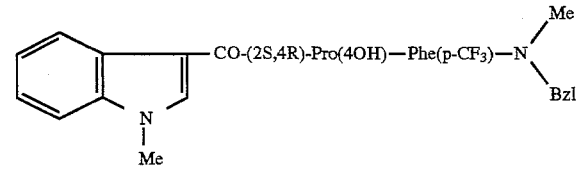 (1-Me-indol-3-yl)—CO-(2S,4R)-Pro(4OH)—Phe(p-CF$_3$)—N(Me)(Bzl) |
| 2-(1) | 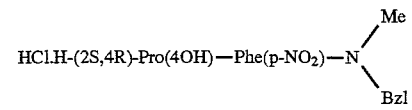 HCl.H-(2S,4R)-Pro(4OH)—Phe(p-NO$_2$)—N(Me)(Bzl) |
| | 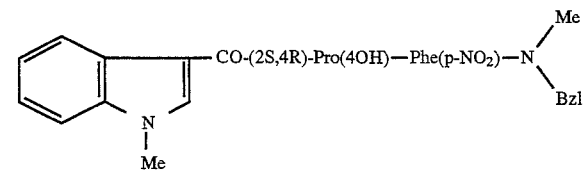 (1-Me-indol-3-yl)—CO-(2S,4R)-Pro(4OH)—Phe(p-NO$_2$)—N(Me)(Bzl) |
| 2-(2) | 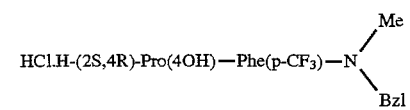 HCl.H-(2S,4R)-Pro(4OH)—Phe(p-CF$_3$)—N(Me)(Bzl) |
| | 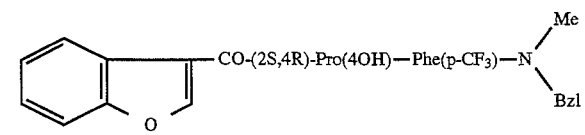 (benzofuran-3-yl)—CO-(2S,4R)-Pro(4OH)—Phe(p-CF$_3$)—N(Me)(Bzl) |

| | |
|---|---|
| 2-(3) | HCl.H-(2S,4R)-Pro(4OH)—Phe(p-CF₃)—N(Me)(Bzl) |
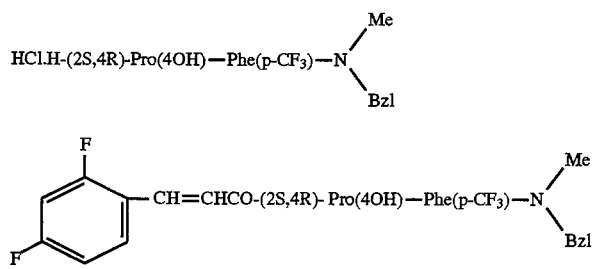
| | |
|---|---|
| 2-(4) | HCl.H-(2S,4R)-Pro(4OH)—Phe(p-NHMs)—N(Me)(Bzl) |
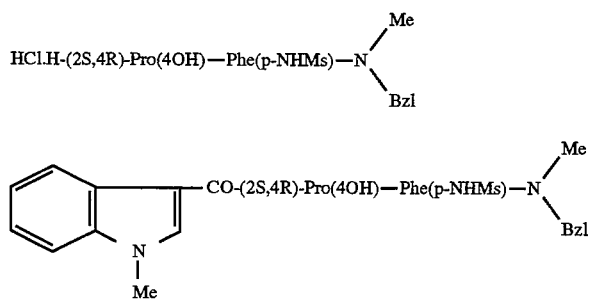
| | |
|---|---|
| 2-(5) | HCl.H-(2S,4R)-Pro(4OH)—Phe(o-F)—N(Me)(Bzl) |
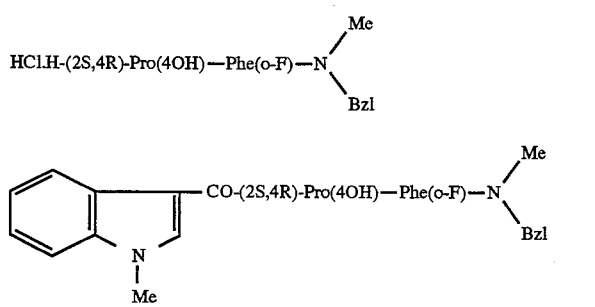
| | |
|---|---|
| 2-(6) | HCl.H-(2S,4R)-Pro(4OH)—Phe(p-F)—N(Me)(Bzl) |
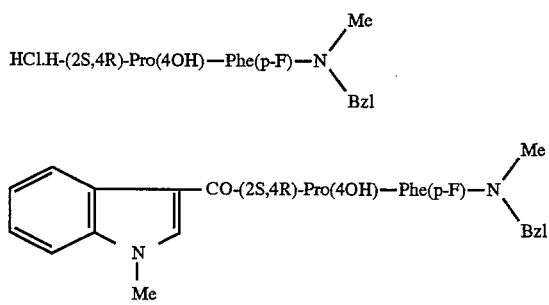
| | |
|---|---|
| 2-(7) | HCl.H-(2S,4R)-Pro(4OH)—Phe(m-F)—N(Me)(Bzl) |
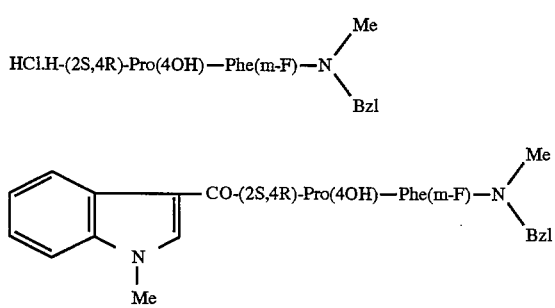
| | |
|---|---|
| 2-(8) | HCl.H-(2S,4R)-Pro(4OH)—Phe(m-CF₃)—N(Me)(Bzl) |

TABLE-continued (indol-1-Me)-CO-(2S,4R)-Pro(4OH)—Phe(m-CF₃)—N(Me)(Bzl)

2-(9) HCl.H-(2S,4R)-Pro(4OH)—Phe(p-OMe)—N(Me)(Bzl)

(indol-1-Me)-CO-(2S,4R)-Pro(4OH)—Phe(p-OMe)—N(Me)(Bzl)

3 HCl.H-(2S,4R)-Pro(4OH)—Phe(p-CF₃)—N(Me)(Bzl)

Ph-CH=CHCO-(2S,4R)-Pro(4OH)—Phe(p-CF₃)—N(Me)(Bzl)

4 HCl.H-(2S,4R)-Pro(4OH)—Phe(p-OCH₂CO₂Et)—N(Me)(Bzl)

(indol-1-H)-CO-(2S,4R)-Pro(4OH)—Phe(p-OCH₂CO₂Et)—N(Me)(Bzl)

5 Boc-Δ(3,4)Pro—Phe(p-CF₃)—N(Me)(Bzl)

(indol-1-Me)-CO-Δ(3,4)Pro—Phe(p-CF₃)—N(Me)(Bzl)

6 (indol-1-H)-CO-(2S,4R)-Pro(4OH)—Phe(p-OCH₂CO₂Et)—N(Me)(Bzl)

(indol-1-H)-CO-(2S,4R)-Pro(4OH)—Phe(p-OCH₂CO₂Na)—N(Me)(Bzl)

TABLE-continued

7

[1-Methylindol-3-yl]—CO-(2S,4R)-Pro(4OH)—Phe(p-NO₂)—N(Me)(Bzl)

[1-Methylindol-3-yl]—CO-(2S,4R)-Pro(4OH)—Phe(p-NH₂)—N(Me)(Bzl)

8

[1-Methylindol-3-yl]—CO-(2S,4R)-Pro(4OH)—Phe(p-NH₂)—N(Me)(Bzl)

[1-Methylindol-3-yl]—CO-(2S,4R)-Pro(4OH)—Phe(p-NH₂)—N(Me)(Bzl) · HCl

9

TFA·H-(2S,4R)-Pro(4OH)—Phe(3,4-diMe)—N(Me)(Bzl)

[1-Methylindol-3-yl]—CO-(2S,4R)-Pro(4OH)—Phe(3,4-diMe)—N(Me)(Bzl)

10

HCl·H-(2S,4R)-Pro(4OH)—Phe(3,4-diMe)—N(Me)(Bzl)

[Pyridin-3-yl]—CH=CHCO-(2S,4R)-Pro(4OH)—Phe(3,4-diMe)—N(Me)(Bzl)

11

[Pyridin-3-yl]—CH=CHCO-(2S,4R)-Pro(4OH)—Phe(3,4-diMe)—N(Me)(Bzl)

[Pyridin-3-yl]—CO-(2S,4R)-Pro(4OH)—Phe(3,4-diMe)—N(Me)(Bzl) · HCl

| | TABLE-continued |
|---|---|
| 12 | HCl.H-(2S,4R)-Pro(4OH)—Phe(3,4-diCl)—N(Me)(Bzl) |
| | 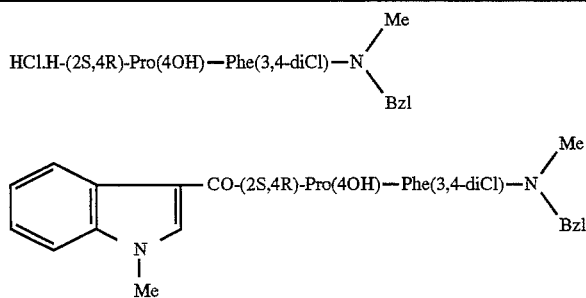 |
| 13 | Boc-(2S,4R)-Pro(4OH)—MePhe(3,4-diMe)—N(Me)(Bzl) |
| | 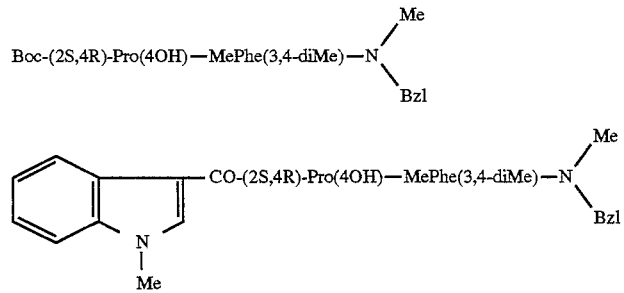 |
| 14 | TFA.H-(2S,4R)-Pro(4OH)—Phe(3,4-diMe)—N(Me)(Bzl) |
| | 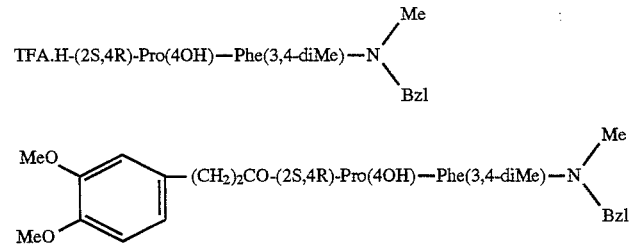 |
| 15 | Boc-(2S,4R)-Pro(4OH)—MePhe(3,4-diMe)—N(Me)(Bzl) |
| | 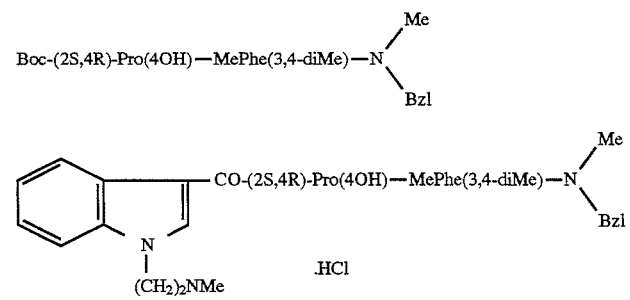 |
| 16 | HCl.H-(2S,4R)-Pro(4OH)—Phe(3,4-diCl)—N(Me)(Bzl) |
| | 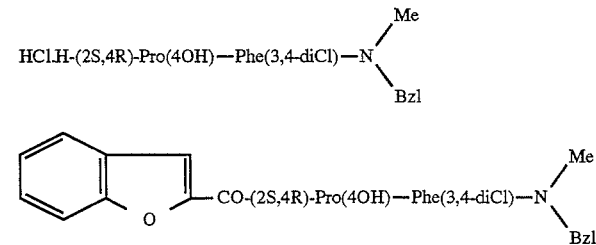 |
| 17 | TFA.H-(2S,4R)-Pro(4OH)—Phe(3,4-diMe)—N(Me)(Bzl) |
| | 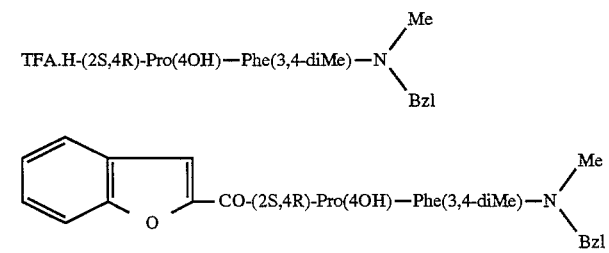 |

PREPARATION 1

To a suspended mixture of Starting Compound (5.0 g) in a mixed solvent of water (35 ml) and acetone (35 ml) was added TEA (4.47 ml) under ice-cooling. To the solution was added a solution of di-tert-butyldicarbonate (5.6 g) in acetone (20 ml), and the solution was stirred at the same temperature for 1 hour and at room temperature for additional 1 hour, during which period, di-tert-butyldicarbonate (1.0 g) was added. After removal of the acetone, water was added and the aqueous solution was washed once with ether. The aqueous layer was then acidified to pH 2 with an addition of 6N hydrochloric acid and was extracted with ethyl acetate. The extract was washed with an aqueous sodium chloride solution and was dried over magnesium sulfate. After evaporation, the residue was crystallized from a mixed solvent of diisopropyl ether and n-hexane, and was collected by filtration and dried to give Object Compound (6.58 g).

mp: 116° C.

IR (Nujol): 3370, 1715, 1690, 1620, 1520 cm$^{-1}$

NMR/DMSO-d$_6$, δ): 1.30 (9H, s), 2.90 (1H) and 3.14 (1H)(ABX,J$_{AB}$=13.7 Hz, J$_{AC}$=4.4Hz, J$_{BC}$=10.7 Hz), 4.17 (1H, m), 7.18 (1H, d, J=8.6 Hz), 7.48 (1H, d, J=8 Hz), 7.65 (1H, d, J=8 Hz)

PREPARATION 2

The object compounds were obtained according to a similar manner to that of Preparation 1.

(1) IR (Neat) : 3320, 2980, 1715, 1510 cm$^{-1}$

NMR (DMSO-d$_6$, δ): 1.26 (s) and 1.31 (s)(9H), 2.7–2.9 (1H, m), 2.9–3.1 (1H, m), 3.9–4.2 (1H, m), 7.0–7.2 (3H, m), 7.2–7.4 (2H, m), 12.63 (1H, broad)

(2) IR (Nujol) : 3380, 1720, 1685, 1520 cm$^{-1}$

NMR (DMSO-d$_6$, δ): 1.24 (s) and 1.30 (s)(9H), 2.7–2.9 (1H, m), 3.0–3.2 (1H, m), 4.0–4.2 (1H, m), 7.0–7.4 (5H, m), 12.67 (1H, broad)

(3) mp: 73°–74° C.

IR (Nujol): 3370, 1715, 1690, 1620, 1580, 1520 cm$^{-1}$

NMR (DMSO-d$_6$, δ): 1.32 (9H, s), 2.92 (1H, d of ABq, J=14 Hz, 10 Hz), 3.06 (1H, d of ABq, J=14 Hz, 5 Hz), 4.0–4.2 (1H, m), 7.0–7.2 (4H, m), 7.3–7.4 (1H, m), 12.51 (1H, br s)

(4) IR (Nujol): 3380, 2660, 2620, 1760, 1640, 1630, 1405 cm$^{-1}$

NMR (DMSO-d$_6$, δ): 1.22 (s) and 1.29 (s)(9H), 2.91 (1H, dd, J=11 Hz, 14 Hz), 3.15 (1H, dd, J=4 Hz, 14 Hz), 4.16 (1H, m), 7.19 (1H, d, J=9 Hz), 7.4–7.7 (4H, m), 12.72 (1H, broad)

PREPARATION 3

To an ice-cooled solution of Starting Compound (2 g), N-methylbenzylamine (0.77 ml), and HOBT (0.81 g) in methylene chloride (50 ml), was added WSC.HCl (1.15 g). The solution was stirred at the same temperature for an hour and at room temperature overnight. After evaporation, the reaction mixture was extracted with ethyl acetate, and the organic layer was washed successively with water, an aqueous sodium hydrogencarbonate solution, 0.5N hydrochloric acid, water and an aqueous sodium chloride solution, and was dried over magnesium sulfate. Evaporation of this solution gave Object Compound (2.88 g).

mp: 86°–88° C.

IR (Nujol) : 3370, 1685, 1640, 1520 cm$^{-1}$

NMR (DSMO-d$_6$, δ): 1.12 (s) and 1.31 (s)(9H), 2.77 and 2.91 (3H, s), 4.4–4.8 (3H, m), 7.1–7.4 (6H, m, 7.4–7.7 (4H, m), 2.8.–3.1 (2H, m)

PREPARATION 4

The following compounds were obtained according to a similar manner to that of Preparation 3.

(1) mp: 110°–111° C.

IR (Nujol): 3390, 1685, 1645, 1600, 1515, 1450, 1345, 1260, 1165 cm$^{-1}$

NMR (DMSO-d$_6$, δ): 1.12 (s) and 1.31 (s)(9H), 2.7–3.1 (5H, m), 4.3–4.8 (3H, m), 7.1–7.5 and 7.5–7.7 and 8.1–8.2 (10H, m)

(2) IR (Neat) : 3320, 2990, 1710, 1640, 1490 cm$^{-1}$

NMR (DMSO-d$_6$, δ): 1.21 (s) and 1.32 (s)(9H), 2.7–3.1 (2H, m), 2.73 (s) and 2.90 (s)(3H), 4.3–4.8 (3H, m), 7.0–7.4 (10H, m)

(3) IR (Nujol) : 3370, 1685, 1635, 1520 cm$^{-1}$

NMR (DMSO-d$_6$, δ): 1.24 (s) and 1.34 (s)(9H), 2.7–3.0 (2H, m), 2.75 (s) and 2.88 (s)(3H), 4.3–4.7 (3H, m), 7.0–7.4 (10H, m)

(4) mp: 94°–96° C.

IR (Nujol): 3380, 1690, 1645, 1635, 1525, 1450, 1250, 1170 cm$^{-1}$

NMR (DMSO-d$_6$, δ): 1.23 (s) and 1.33 (9H, s), 2.7–2.9 (5H, m), 4.3–4.7 (3H, m), 6.9–7.4 (10H, m)

(5) IR (Nujol) : 3370, 1685, 1640, 1520 cm$^{-1}$

NMR (DMSO-d$_6$, δ): 1.19 (s) and 1.30 (s)(9H), 2.77 (s), and 2.91 (s)(3H), 2.8–3.1 (2H, m), 4.3–4.8 (3H, m), 7.0–7.7 (10H, m)

(6) IR (Nujol) : 3320, 1685, 1640, 1530, 1515, 1455, 1415, 1265, 1170 cm$^{-1}$ (DMSO-d$_6$, δ): 1.2–1.4 (9H, m), 2.6–2.9 (5H, m), 4.3–4.7 (3, m), 6.5–6.7 and 5.8–6.9 and 6.9–7.4 (10H, m), 9.20 (1H, s)

PREPARATION 5

To a solution of Starting Compound (1.54 g) in THF (30 ml) were added sodium hydride (60% in oil, 176 mg) and methyl iodide (0.5 ml). The mixture was stirred at 60° C. for an hour. After concentration, the product was extracted with ethyl acetate, and the organic layer was washed successively with water and an aqueous sodium chloride solution and was dried over magnesium sulfate. Evaporation of this solution gave Object Compound (1.78 g) as an oil.

IR (CHCl$_3$) : 3320, 1705, 1640, 1510, 1450, 1365, 1250, 1170 cm$^{-1}$

NMR (DMSO-d$_6$, δ): 1.2–1.4 (9H, m), 2.7–2.9 (5H, m), 3.70 (s) and 3.72 (s)(3H), 4.3–4.6 (3H, m), 6.7–6.9 (2H, m), 7.0–7.4 (8H, m)

PREPARATION 6

To an ice-cooled solution of Starting Compound (2.05 g) in methylene chloride (20 ml) was added 4N-HCL/DOX (19.0 ml). The solution was stirred at the same temperature for 5 minutes. Then the cooling bath was removed and the solution was stirred at room temperature for an hour. After evaporation, the residue was triturated with diisopropyl ether, collected by filtration, and dried over sodium hydroxide in vacuo to give Object Compound (1.68 g).

mp: 159° C.

IR (Nujol): 1650, 1605, 1580, 1495, 1335 cm$^{-1}$

NMR (DMSO-d$_6$, δ): 2.73 (3H, s), 3.1–3.3 (2H, m), 4.1–4.8 (3H, m), 7.1–7.2 (2H, m), 7.2–7.4 (3H, m), 7.37 (2H, d, J=8 Hz), 7.62 (d, J=8 Hz) and 7.69 (d, J=8 Hz)(2H), 8.51 (2H, broad s)

PREPARATION 7

The object compounds were obtained according to a similar manner to that of Preparation 6.

(1) IR (CHCl$_3$): 1655, 1605, 1525, 1350, 1215 cm$^{-1}$

NMR (DMSO-d$_6$, δ): 2.72 (s) and 2.74 (s)(3H), 3.1–3.3 (2H, m), 4.1–4.8 (3H, m), 7.1–7.3 (5H, m), 7.52 (2H, d, J=8 Hz), 8.1–8.2 (2H, m), 8.61 (3H, br s)

(b 2) IR (CHCl$_3$): 1655, 1640, 1610, 1510, 1490, 1450, 1400, 1330, 1215 cm$^{-1}$

NMR (DMSO-d$_6$, δ): 2.64 (s) and 2.70 (s)(3H), 2.9–3.2 (5H, m), 4.3–4.7 (3H, m), 7.1–7.2 and 7.3–7.4 (9H, m), 8.47 (3H, br s), 9.8–9.9 (1H, m)

(3) IR (CHCl$_3$): 1655, 1590, 1490, 1450, 1255, 1215 cm$^{-1}$

NMR (DMSO-d$_6$, δ): 2.71 (s) and 2.73 (3H, s), 3.0–3.3 (2H, m), 4.1–4.8 (3H, m), 7.0–7.2 and 7.2–7.4 (9H, m), 8.49 (3H, br s)

(4) IR (Nujol) : 3500, 3450, 1650, 1610 cm$^{-1}$

NMR (DMSO-d$_6$, δ) : 2.70 (s) and 2.75 (s)(3H), 3.1–3.3 (2H, m), 4.09 and 4.67 (ABq, J=16 Hz) and 4.46 (s)(2H), 4.75 (1H, t, J=7 Hz), 7.0–7.2 (2H, m), 7.2–7.4 (3H, m), 7.5–7.6 (2H, m), 7.6–7.7 (2H, m), 8.49 (3H, broad s)

(5) IR (CHCl$_3$): 1660, 1650, 1615, 1515, 1250, 1220 cm$^{-1}$

NMR (DMSO-d$_6$, δ): 2.59 (s) and 2.69 (s)(3H), 2.9–3.2 (2H, m), 3.72 (s) and 3.76 (s)(3H), 4.3–4.5 (3H, m), 6.75–6.95 (2H, m), 7.1–7.2 and 7.3–7.4 (7H, m), 8.50 (3H, br s)

PREPARATION 8

To an ice-cooled solution of Starting Compound (1.65 g), Boc-(2S,4R)-Pro(4OH)-OH (1.02 g) and HOBT (0.60 g) in a mixed solvent of methylene chloride (45 ml) and dimethylformamide (10 ml) was added WSC (0.80 ml). The solution was stirred at the same temperature for an hour and at room temperature overnight. After evaporation, the reaction mixture was extracted with ethyl acetate and the organic layer was washed successively with an aqueous sodium hydrogencarbonate solution, water, 0.5N hydrochloric acid, water and an aqueous sodium chloride solution, and was dried over magnesium sulfate and evaporated in vacuo to give Object Compound (2.35 g) as an oil.

IR (CHCl$_3$): 1700, 1685, 1665, 1645, 1635, 1555, 1540 cm$^{-1}$

NMR (DMSO-d$_6$, δ) : 1.1–1.3 (m) and 1.65 (s)(9H), 1.5–1.8 (1H, m), 1.8–2.1 (1H, m), 2.9 (3H, s), 2.7–3.1 (2H, m), 3.1–3.4 (1H, m), 3.4–3.5 (1H, m), 4.1–4.3 (2H, m), 4.3–4.5 (2H, m), 4.7–5.1 (2H, m), 7.0–7.7 (9H, m), 8.39 (1H, d, J=8 Hz)

PREPARATION 9

The object compounds were obtained according to a similar manner to that of Preparation 8.

(1) IR (Neat) : 3300, 2990, 1705, 1690, 1640 cm$^{-1}$

NMR (DMSO-d$_6$, δ): 1.21 (s) and 1.40 (s)(9H), 2.7–3.2 (5H, m), 3.9–4.3 (2H, m), 4.3–5.1 (4H, m), 5.4–5.6 (1H, m), 5.9–6.0 (1H, m), 7.0–7.1 (2H, m), 7.0–7.1 (4H, m) 7.4–7.7 (3H, m), 8.4–8.6 (1H, m)

(2) IR (CHCl$_3$): 1690–1630, 1605, 1520, 1455, 1345, 1160 cm$^{-1}$

NMR (DMSO-d$_6$, δ): 1.12 (s), 1.22 (s) and 1.37 (s) (9H), 1.5–1.8 (1H, m), 1.8–2.1 (1H, m), 2.7–3.1 (5H, m), 3.1–3.5 (2H, m), 4.0–4.3 (2H, m), 4.3–4.6 (2H, m), 4.7–5.2 (2H, m), 7.0–7.5 (m), 7.5–7.7 (m), 8.0–8.2 (m) and 8.32 (s)(9H), 8.42 (1H, d, J=8 Hz)

(3) IR (CHCl$_3$): 1690, 1680, 1630, 1510, 1400, 1330, 1155 cm$^{-1}$

NMR (DMSO-d$_6$, δ): 1.26 (s) and 1.39 (s)(9H), 1.5–1.8 (1H, m), 1.8–2.1 (1H, m), 2.7–3.1 (8H, m), 3.2–3.3 (1H, m), 3.3–3.5 (1H, m), 4.1–4.3 (2H, m), 4.3–5.1 (4H, m), 6.9–7.1 and 7.1–7.4 (9H, m), 8.2–8.4 (1H, m), 9.63 (1H, br s)

(4) IR (CHCl$_3$): 3400–3200, 1690, 1680, 1640, 1590, 1550, 1450, 1410, 1365, 1250 cm$^{-1}$

NMR (DMSO-d$_6$, δ) : 1.22 (s) and 1.38 (9H, s), 1.5–1.8 (1H, m), 1.8–2.1 (1H, m), 2.7–3.1 (5H, m), 3.1–3.3 (1H, m), 3.3–3.5 (1H, m), 4.1–4.3 (2H, m), 4.4–4.6 (2H, m), 4.8–5.1 (2H, m), 6.8–7.4 (9H, m), 8.3–8.4 (1H, m)

(5) IR (Neat) : 3450–3300, 1690–1650, 1640 cm$^{-1}$

NMR (DMSO-d$_6$, δ): 1.19 (s), 1.21 (s) and 1.38 (s)(9H), 1.6–1.8 (1H, m), 1.8–2.1 (1H, m), 2.7–3.5 (7H, m), 4.0–4.2 (2H, m), 4.3–4.7 (2H, m), 4.7–5.1 (2H, m), 7.0–7.2 (2H, m), 7.2–7.7 (7H, m), 8.3–8.5 (1H, m)

(6) IR (CHCl$_3$): 3450–3300, 1695–1630, 1510, 1405, 1250, 1160 cm$^{-1}$

NMR (DMSO-d$_6$, δ) : 1.25 (s) and 1.39 (s)(9H), 1.5–1.8 (1H, m), 1.8–2.1 (1H, m), 2.7–3.0 (5H, m), 3.2–3.3 (1H, m), 3.4–3.5 (1H, m), 3.71 (3H, s), 4.1–4.3 (2H, m), 4.3–4.6 and 4.7–5.0 (4H, m), 6.7–6.9 (2H, m), 6.9–7.1 and 7.1–7.3 (7H, m), 8.2–8.4 (1H, m)

PREPARATION 10

To a solution of Starting Compound (2.5 g) in methanol (70 ml) was added 10% palladium on charcoal (0.5 g), and the mixture was hydrogenated under atmospheric pressure at room temperature for 1.5 hours. Filtration and concentration of the mixture gave Object Compound (2.27 g) as an amorphous solid.

IR (CHCl$_3$) : 3370, 1705, 1640, 1520, 1365, 1290, 1250, 1170 cm$^{-1}$

NMR (DMSO-d$_6$, δ): 1.1–1.4 (9H, m), 2.5–2.9 (5H, m), 4.3–4.6 (3H, m), 4.91 (2H, s), 6.4–6.5 (2H, m), 6.74 (1H, d, J=8 Hz), 6.89 (1H, d, J=8 Hz), 7.0–7.2 and 7.2–7.4 (6H, m)

PREPARATION 11

To an ice-cooled solution of Starting Compound (1.75 g) in pyridine (35 ml) was added methanesulfonyl chloride (0.39 ml). The solution was stirred for an hour at the same temperature. After concentration, the product was extracted with ethyl acetate and the organic layer was washed successively with water, diluted aqueous sodium hydrogen carbonate solution, water, 0.5N hydrochloric acid and sodium chloride solution, and was dried over magnesium sulfate. Evaporation of the extract gave Object Compound (2.14 g) as an amorphous solid.

IR (CHCl$_3$): 1710–1690, 1635, 1510, 1495, 1400, 1335, 1250 cm$^{-1}$

NMR (DMSO-d$_6$, δ): 1.26 (s) and 1.34 (s)(9H), 2.7–2.9 (5H, m), 2.92 (3H, s), 4.4–4.7 (3H, m), 7.0–7.4 (10H, m), 9.62 (1H, s)

PREPARATION 12

The object compounds were obtained according to similar manner to that of Preparation 6 and Preparation 8, successively.

(1) IR (Neat) : 3400, 3320, 1680 (broad), 1640, 1490 cm$^{-1}$

NMR (DMSO-d$_6$, δ): 1.24 (s) and 1.39 (s)(9H), 1.5–1.8 (1H, m), 1.8–2.1 (1H, m), 2.7–3.5 (7H, m), 4.1–4.3 (2H, m), 4.4–4.8 (2H, m), 4.9–5.2 (2H, m), 7.0–7.4 (9H, m), 8.2–8.5 (1H, m)

(2) IR (Neat): 3450–3300 (broad), 1690–1660 (broad), 1640, 1510 cm$^{-1}$

NMR (DMSO-d$_6$, δ): 1.23 (s) and 1.39 (s)(9H), 1.5–1.8 (1H, m), 1.8–2.1 (1H, m), 2.7–3.1 (5H, m), 3.1–3.5 (2H, m), 4.0–4.3 (2H, m), 4.3–5.1 (4H, m), 7.0–7.4 (9H, m), 8.35 (1H, d, J=8 Hz)

(3) IR (Nujol) : 3280, 1665, 1630, 1515 cm$^{-1}$

NMR (DMSO-d$_6$, δ): 1.28 (s) and 1.39 (s)(3H), 1.60–1.90 (1H, m), 1.90–2.10 (1H, m), 2.60–3.00 (2H, m), 2.75 (s) and 2.85 (s)(3H), 3.20–3.30 (1H, m), 3.35–3.50 (1H, m), 4.10–4.70 (4H, m) 4.70–5.05 (2H, m), 6.60 (d, J=8 Hz) and 6.64 (d, J=8 Hz)(2H), 6.86 (d, J=8 Hz) and 7.03 (d, J=8 Hz)(2H), 6.90–7.10 (2H, m), 7.20–7.35 (3H, m), 8.20–8.40 (1H, m), 9.19 (s) and 9.23 (s)(1H)

PREPARATION 13

To a solution of Starting Compound (5.0 g) in methylene chloride (120 ml) were added cetyltrimethylammonium chloride (300 mg) and powdered sodium hydroxide (0.80 g). Then, ethyl bromoacetate (2.02 g) was added to the mixture and the mixture was stirred for two hours at room temperature. After addition of acetic acid (1 ml) and concentration, ethyl acetate and water were added to the residue. The separated aqueous layer was extracted with ethyl acetate again and the organic layers were combined and washed successively with an aqueous sodium hydrogencarbonate solution, 0.5N hydrochloric acid, and an aqueous sodium chloride solution, and dried over magnesium sulfate. Concentration of this solution gave crude product (3.83 g), which was purified on a silica gel column eluting with a mixed solvent of methylene chloride and methanol (97:3 to 94:6) to give Object Compound (3.13 g) as an amorphous solid.

IR (CH$_2$Cl$_2$): 3600, 3400, 1750, 1680, 1640 cm$^{-1}$

NMR (CDCl$_3$, δ): 1.30 (3H, t), 1.45 (9H, s), 1.8–2.2 (2H, m), 2.71 and 2.91 (3H, s), 2.9–3.1 (3H, m), 3.3–3.55 (2H, m), 4.26 (2H, q), 4.0–4.5 (4H, m), 4.55–4.6 (3H, m), 5.1–5.2 (1H, m), 6.7–6.8 (2H, m), 7.0–7.2 (4H, m), 7.25–7.3 (3H, m)

PREPARATION 14

To an ice-cooled solution of Starting Compound (1.1 g) in methylene chloride (11 ml) was added 4N-HCl/DOX (8.1 ml). The solution was stirred at the same temperature for 5 minutes and at room temperature for 50 minutes. After evaporation, the residue was triturated with diisopropyl ether, collected by filtration and dried to give Object Compound (0.88 g).

IR (Nujol) : 3250, 1670, 1645, 1580, 1555 cm$^{-1}$

NMR (DMSO-d$_6$, δ): 1.6–1.9 (1H, m), 2.2–2.4 (1H, m), 2.79 (s) and 2.89 (s)(3H), 2.9–3.4 (4H, m), 4.2–4.6 (4H, m), 4.9–5.2 (1H, m), 5.5–5.6 (1H, m), 7.0–7.7 (10H, m), 9.23 (1H, d, J=8 Hz)

PREPARATION 15

The object compounds were obtained according to a similar manner to that of Preparation 14.

(1) mp: 188°–189° C.

IR (Nujol): 3500, 3290, 2700, 1665, 1645, 1605, 1565, 1515, 1345 cm$^{-1}$

NMR (DMSO-d$_6$, δ): 1.6–1.9 (1H, m), 2.1–2.4 (1H, m), 2.7–3.4 (7H, m), 4.1–4.7 (4H, m), 4.9–5.2 (1H, m), 5.5–5.6 (1H, m), 7.0–7.6 (7H, m), 8.0–8.2 (2H, m), 8.51 (br s) and 10.0 (br s)(1H), 9.25 (1H, d, J=8 Hz )

(2) IR (CHCl$_3$) : 3320, 3020, 2850, 2700, 1660, 1640, 1630, 1530, 1510, 1390, 1215 cm$^{-1}$

NMR (DMSO-d$_6$, δ): 1.7–1.9 (1H, m), 2.2–2.4 (1H, m), 2.7–3.2 (8H, m), 3.2–3.4 (2H, m), 4.2–4.7 and 4.9–5.1 (6H, m), 7.0–7.2 and 7.2–7.4 (9H, m), 8.67 (1H, br s), 9.16 (1H, d, J=8 Hz), 9.7–9.8 (1H, m), 9.98 (1H, br s)

(3) NMR (DMSO-d$_6$, δ): 1.6–1.9 (1H, m), 2.2–2.4 (1H, m), 2.75 (s) and 2.86 (s)(3H), 2.8–3.4 (4H, m), 4.2–4.7 (4H, m), 5.0–5.2 (1H, m), 5.57 (1H, s), 7.0–7.4 (9H, m), 8.62 (1H, broad), 9.23 (1H, d, J=8 Hz), 10.00 (1H, broad)

(4) NMR (DMSO-d$_6$, δ): 1.6–1.9 (1H, m), 2.2–2.4 (1H, m), 2.77 (s) and 2.86 (s)(3H), 2.8–3.2 (3H, m), 3.2–3.5 (1H, m), 4.2–4.7 (4H, m), 4.8–5.1 (1H, m), 5.56 (1H, s), 7.0–7.4 (9H, m), 8.58 (1H, broad), 9.17 (1H, d, J=8 Hz), 9.98 (1H, broad)

(5) mp: 216°–217° C.

IR (Nujol): 3410, 3200, 3070, 1675, 1640, 1615, 1560, 1450, 1265 cm$^{-1}$

NMR (DMSO-d$_6$, δ): 1.7–1.9 (1H, m), 2.2–2.4 (1H, m), 2.7–3.2 and 3.2–3.4 (7H, m), 4.2–4.7 (4H, m), 4.9–5.1 (1H, m), 5.58 (1H, s), 6.9–7.4 (9H, m), 8.58 (1H, br s), 9.1–9.3 (1H, m), 10.03 (1H, br s)

(6) mp: 137°–141° C.

IR (Nujol) : 3300, 1750, 1670, 1640, 1560, 1510. cm$^{-1}$

NMR (DMSO-d$_6$, δ): 1.21 (3H, t, J=7 Hz), 1.7–1.9 (1H, m), 2.2–2.4 (1H, m), 2.74 and 2.83 (3H, s), 2.8–3.1 (2H, m), 3.2–3.4 (2H, m), 4.16 (2H, q, J=7 Hz), 4.3–4.6 (4H, m), 4.74 (2H, s), 4.8–5.0 (1H, m), 5.59 (1H, m), 6.8–6.9 (2H, m), 7.05–7.4 (7H, m), 9.16 (1H, d, J=7.7 Hz)

(7) NMR (DMSO-d$_6$, δ): 1.7–1.9 (1H, m), 2.2–2.4 (1H, m), 2.78 (s) and 2.89 (s)(3H), 2.9–3.4 (4H, m), 4.2–4.7 (4H, m), 4.9–5.1 (1H, m), 5.58 (1H, d, J=3 Hz), 7.0–7.2 (2H, m), 7.2–7.4 (3H, m), 7.4–7.7 (4H, m), 9.20 (1H, d, J=8 Hz)

(8) IR (CHCl$_3$) : 1675, 1635, 1550, 1510, 1450, 1300, 1250, 1180 cm$^{-1}$

NMR (DMSO-d$_6$, δ): 1.7–1.9 (1H, m), 2.2–2.4 (1H, m), 2.7–3.1 and 3.2–3.4 (7H, m), 3.72 (3H, s), 4.2–4.6 (4H, m), 4.8–5.0 (1H, m), 5.57 (1H, br s), 6.8–6.9 (2H, m), 7.0–7.4 (7H, m), 8.59 (1H, br s), 9.13 (1H, d, J=8 Hz), 10.04 (1H, br s)

PREPARATION 16

The object compound was obtained according to a similar manner to that of Preparation 1.

IR (CHCl$_3$): 3470, 1725, 1715, 1500 cm$^{-1}$

NMR (DMSO-d$_6$, δ): 1.33 (9H, s), 2.17 (6H, s), 2.65–3.0 (2H, m), 3.95–4.1 (1H, m), 6.9–7.05 (4H, m), 12.46 (1H, br s)

PREPARATION 17

The object compound was obtained according to a similar manner to that of Preparation 3.

IR (Neat) : 3450, 3320, 1710, 1640, 1365 cm$^{-1}$

NMR (DMSO-d$_6$, δ): 1.2–1.4 (9H, m), 2.1–2.2 (6H, m), 2.65–2.95 (5H, m), 4.3–4.7 (3H, m), 6.75–7.4 (9H, m)

PREPARATION 18

The object compound was obtained according to a similar manner to that of Preparation 6.

mp: 96°–104° C.

IR (Nujol) : 3440, 1650, 1610, 1490, 1450, 1280 cm$^{-1}$

NMR (DMSO-d$_6$, δ) : 2.1–2.25 (6H, m), 2.62 (s) and 2.69 (3H, s), 2.85–3.2 (2H, m), 4.0–4.1 and 4.35–4.65 (3H, m), 6.9–7.4 (8H, m), 8.49 (3H, br s)

PREPARATION 19

The object compound was obtained according to a similar manner to that of Preparation 8.

IR (CHCl$_3$) : 3450–3300, 1690–1650, 1645–1625, 1450, 1155 cm$^{-1}$

NMR (DMSO-d$_6$, δ): 1.2–1.45 (9H, m), 1.6–1.85 (1H, m), 1.9–2.2 (7H, m), 2.7–3.0 (5H, m), 3.15–3.5 (2H, m), 4.1–5.1 (6H, m), 6.7–7.35 (8H, m), 8.25–8.35 (1H, m)

PREPARATION 20

The object compound was obtained according to a similar manner to that of Preparation 14 excepting for using TFA in place of 4N-HCl/DOX.

IR (CHCl$_3$): 3450–3200, 1680, 1640, 1565, 1455 cm$^{-1}$

NMR (DMSO-d$_6$, δ): 1.7–1.9 (1H, m), 2.1–2.4 (7H, m), 2.65–3.15 (5H, m), 3.25–3.5 (2H, m), 4.2–5.1 and 5.55–5.65 (6H, m), 6.8–7.4 (8H, m), 9.1–9.3 (1H, m), 8.65 (1H, br s), 10.0 (1H, br s)

PREPARATION 21

To a suspended mixture of Starting Compound (18.0 g) in water (90 ml) was added 1N aqueous sodium hydroxide solution (65.8 ml). The solution was warmed to 37° C. and the pH was adjusted to 8.0 by an addition of 1N hydrochloric acid. Then cobalt(II) chloride hexahydrate (90 mg) and acylase (trademark: Acylase Amano 15000) (900 mg) were added to the solution. The reaction mixture was stirred at 37° C. overnight, during which period the pH was maintained at 7.5 by an addition of 1N aqueous sodium hydroxide solution. The precipitates were collected by filtration, washed with water, and dried to give Object Compound (4.75 g).

mp:>192° C.

IR (Nujol): 3400, 1605, 1584, 1512, 888, 840 cm$^{-1}$

NMR (D$_2$O+NaOD, δ): 2.65–3.15 (2H, m), 3.49 (1H, dd, J=7.38 Hz, 5.72 Hz), 7.12 (1H, dd, J=8.24 Hz, 1.70 Hz), 7.36 (1H, d, J=1.6 Hz), 7.42 (1H, d, J=8.22 Hz)

PREPARATION 22

To an ice-cooled solution of Starting Compound (4.58 g) and methyl iodide (7.8 ml) in THF (40 ml) was added 60% sodium hydride (1.87 g) under nitrogen atmosphere. The mixture was stirred at room temperature overnight. Water was added to the mixture and THF was evaporated. Ether and water were added and the aqueous layer was separated. The organic layer was washed with water again. These aqueous layers were combined and acidified with 6N hydrochloric acid to pH 2 and the separated oil was extracted with ethyl acetate. The extract was washed with an aqueous sodium chloride solution, dried over magnesium sulfate and evaporated to give Object Compound as an oil (4.20 g).

IR (CHCl$_3$): 2600, 1700 cm$^{-1}$

NMR (CDCl$_3$, δ): 1.34 and 1.41 (9H, s); 2.22 (6H, s), 2.69 and 2.76 (3H, s); 2.9–3.3 (2H, m); 4.64 (dd, J=10.9 Hz and 4.5 Hz) 4.82 (dd, J=10.7 Hz and 5.2 Hz)} (1H); 6.9–7.1 (3H, m), 8.83 (1H, s)

PREPARATION 23

The object compound was obtained according to a similar manner to that of Preparation 1.

mp: 119.0°–121.5° C.

IR (Nujol) : 3370, 1718, 1690, 1526, 818 cm$^{-1}$

NMR (DMSO-d$_6$, δ): 1.26, 1.31 (9H, s); 2.70–3.15 (2H, m); 4.00–4.10 (1H, m); 7.10–7.30, 7.45–7.60 (4H, m); 12.70 (1H, br s)

PREPARATION 24

To an ice-cooled solution of Starting Compound (5.00 g) in methylene chloride (50 ml) were added TEA (2.29 ml) and pivaloyl chloride (2.03 ml). The mixture was stirred for 35 minutes at the same temperature and N-methylbenzylamine (1.81 g) was added to the solution. The solution was stirred for 25 minutes under ice-cooling and for additional 1.5 hours. After concentration, water and ethyl acetate were added to the residue and the separated organic layer was washed successively with an aqueous sodium hydrogen carbonate solution, water, 0.5N hydrochloric acid, and an aqueous sodium chloride solution, and dried over magnesium sulfate. After concentration, the crystalline residue (7.10 g) was washed with diisopropyl ether, collected by filtration and dried to give Object Compound (5.29 g).

mp: 103.0°–106° C.

IR (Nujol): 3390, 1690, 1638, 814, 730, 710 cm$^{-1}$

NMR (DMSO-d$_6$, δ): 1.21, 1.32 (9H, s); 2.90, 2.94 (3H, s); 2.70–3.05 (2H, m); 4.40–4.75 (3H, m); 7.05–7.65 (9H, m)

PREPARATION 25

The object compound was obtained according to a similar manner to that of Preparation 3.

mp: 126°–127° C.

IR (Nujol) : 1680, 1645 cm$^{-1}$

NMR (CDCl$_3$, δ): 1.05, 1.19, 1.22 and 1.37 (9H, s); 2.18, 2.20 and 2.22 (6H, s); 2.83, 2.85 and 2.89 (6H, s); 2.9–3.25 (2H, m); 4.36–4.75 (2H, m); 4.95–5.03 and 5.30–5.45 (1H, m); 6.85–7.3 (8H, m)

PREPARATION 26

To an ice-cooled solution of Starting Compound (2.00 g) in ethyl acetate (7.5 ml) was added a solution (15 ml) of 4N-hydrochloric acid in ethyl acetate. The solution was stirred at the same temperature for 35 minutes and concentrated. Methylene chloride and an aqueous sodium hydrogen carbonate were added to the residue, and the organic layer was separated, was dried over magnesium sulfate, and concentrated to 5 ml volume (Solution I).

To an ice-cooled solution of Boc-(2S,4R)-Pro(4OH)-OH (1.06 g) in methylene chloride (15 ml) in another reaction vessel were added TEA (0.70 ml) and pivaloyl chloride (0.62 ml), and the mixture was stirred for 15 minutes at the same temperature. To this solution was added the solution prepared above (Solution I), and the resulting solution was stirred for an hour under ice-cooling and was left standing overnight at room temperature. N,N-Dimethyl-1,3-propanediamine (0.23 ml) was added to the solution, and the mixture was stirred for an hour at room temperature. After concentration, ethyl acetate and water were added to the residue and the organic layer was washed successively with an aqueous sodium hydrogencarbonate solution, water, 0.5N hydrochloric acid, water and an aqueous sodium chloride solution, and was dried over magnesium sulfate. Evaporation of the solvent gave Object Compound (2.43 g) as an amorphous solid.

IR (CHCl$_3$): 3400–3260, 2960, 2930, 1625 cm$^{-1}$

NMR (DMSO-d$_6$, δ): 1.19, 1.38 (9H, s); 1.50–2.10 (2H, m),2.70–3.10 (5H, m); 3.15–3.50 (2H, m); 4.05–5.05 (6H, m); 7.00–7.65 (8H, m); 8.25–8.40 (1H, m)

MASS: M$^+$: 550

PREPARATION 27

The object compound was obtained according to a similar manner to that of the former half of Preparation 26.

mp: 219°–221° C.

IR (Nujol) : 2750, 1650, 1550 cm$^{-1}$

NMR (DMSO-d$_6$, δ): 2.15 (3H, s), 2.19 (3H, s), 2.5 (6H, m), 2.85–3.0 (1H, m), 3.17–3.35 (1H, m), {3.97 (J=16.2 Hz) and 4.33 (J=16.2 Hz) 4.39 (J=14.7 Hz) and 4.51 (J=14.7 Hz)}(1H), 4.65 (1H, dd, J=4.5 Hz, 9.3 Hz), 6.9–7.1 (5H, m), 7.3 (3H, m), 9.5 (2H, br)

PREPARATION 28

The object compound was obtained according to a similar manner to that of the latter half of Preparation 26.

IR (CHCl$_3$) : 3450, 1690, 1660 (sh), 1640 cm$^{-1}$

NMR (DMSO-d$_6$, δ): 1.09, 1.21, 1.27, 1.28, 1.37 and 1.38 (9H, s), 1.2–1.4, 1.4–1.6, 2.0–2.2 (2H, m), 1.99 and 2.13 (6H, s), 2.6–2.8 (4H, m), 3.0 (3H, m), 3.2–3.45 (3H, m), 4.1–4.7 (4H, m), 5.0 (1H, m), 5.4–5.6 (1H, m), 6.8–7.3 (8H, m)

PREPARATION 29

To an ice-cooled solution of Starting Compound (2.20 g) in ethyl acetate (7.5 ml) was added a solution (15 ml) of 4N-hydrogen chloride in ethyl acetate. The solution was stirred at the same temperature for two hours. After concentration, the residue was crystallized from ether to give Object Compound (1.59 g).

mp: 168.0°–175.0° C.

IR (Nujol) : 3270, 1640 cm$^{-1}$

NMR (DMSO-d$_6$, δ): 1.60–1.90, 2.10–2.40 (2H, m), 2.80, 2.93 (3H, s), 2.70–3.40 (4H, m), 4.05–4.75 (4H, m), 4.85–5.10 (1H, m), 5.50–5.60 (1H, m), 7.00–7.65 (8H, m), 8.30–8.80, 9.60–10.15 (2H, br s), 9.17 (1H, d, J=8.08 Hz)

EXAMPLE 1

To an ice-cooled solution of 1-methylindole-3-carboxylic acid (0.23 g), Starting Compound (0.63 g), methylene chloride (12 ml) and HOBT (0.18 g) was added WSC (0.24 ml). The solution was stirred at the same temperature for an hour and at room temperature overnight. After evaporation, the reaction mixture was extracted with ethyl acetate and the organic layer was washed successively with an aqueous sodium hydrogencarbonate solution, water, 0.5N hydrochloric acid, water, and an aqueous sodium chloride solution, and dried over magnesium sulfate. After evaporation, the residue was purified on a silica gel column (100 g) eluting with a mixed solvent of chloroform and methanol (50:1). The fractions containing the desired compound were collected and evaporated. The residue was then crystallized from ethyl acetate, filtered collected by filtration and dried to give Object Compound (0.50 g).

mp: 183°–184° C.

IR (Nujol): 3270, 1680, 1655, 1580, 1570, 1530 cm$^{-1}$

NMR (DMSO-d$_6$, δ): 1.7–1.9 (1H, m), 1.9–2.1 (1H, m), 2.72 (s) and 2.85 (s)(3H), 2.9–3.3 (2H, m), 3.66 (1H, d, J=5 Hz), 3.8–4.1 (1H, m), 3.85 (3H, s), 4.30 (s) and 4.43 (s) and 4.6–4.8 (m)(4H) 4.9–5.2 (2H, m), 7.0–7.7 (12H, m), 7.88 (1H, s), 8.07 (1H, d, J=8 Hz), 8.4–8.7 (1H, m)

EXAMPLE 2

The object compounds were obtained according to a similar manner to that of Example 1.

mp: 183°–184° C.

IR (Nujol): 3280, 1690, 1650, 1585, 1545, 1520, 1450, 1350 cm$^{-1}$

NMR (DMSO-d$_6$, δ): 1.7–1.9 (1H, m), 1.9–2.1 (1H, m), 2.6–3.3 (5H, m), 3.5–3.7 (1H, m), 3.7–4.0 (1H, m), 3.85 (3H, s), 4.2–4.7 (4H, m), 4.9–5.1 (2H, m), 7.0–7.6 (10H, m), 7.8–8.1 (4H, m), 8.4–8.6 (1H, m)

(2) mp: 124°–126° C.

IR (Nujol): 3420, 3300, 1670, 1640, 1615, 1545, 1325, 1160, 1126, 1110, 1066 cm$^{-1}$ NMR (DMSO-d$_6$, δ): 1.6–2.4 (2H, m), 2.6–3.3 (5H, m), 3.6–4.1 (2H, m), 4.2–4.8 (4H, m), 5.0–5.2 (2H, m), 6.8–7.9 (14H, m), 8.6–8.9 (1H, m)

(3) mp: 98°–100° C.

IR (Nujol): 3300, 1650, 1630, 1614, 1588, 1530, 1504, 1330 cm$^{-1}$

NMR (DMSO-d$_6$, δ): 1.6–2.2 (2H, m), 2.5–3.2 (5H, m), 3.5–3.9 (2H, m), 4.2–4.8 (4H, m), 4.9–5.2 (2H, m), 6.7–6.8, 7.0–7.6, 7.7–7.8, 8.0–8.2, 8.5–8.6 and 8.9–9.0 (14H, m)

(4) IR (CHCl$_3$) : 1640, 1630, 1530, 1510, 1465, 1435, 1330, 1220, 1150 cm$^{-1}$

NMR (DMSO-d$_6$, δ): 1.7–1.9 (1H, m), 1.9–2.1 (1H, m), 2.6–3.1 (5H, m), 2.89 (3H, s), 3.6–3.7 (1H, m), 3.8–4.0 (1H, m), 3.86 (3H, s), 4.2–4.6, 4.6–4.8 and 4.8–5.1 (6H, m), 7.0–7.5 (12H, m), 7.8–8.0 (1H, m), 8.06 (1H, d, J=8 Hz), 8.3–8.5 (1H, br s), 9.64 (1H, br s)

(5) IR (Nujol) : 3420, 3290, 3100, 1655, 1640, 1600, 1570, 1535 cm$^{-1}$

NMR (DMSO-d$_6$, δ): 1.7–1.9 (1H, m), 1.9–2.1 (1H, m), 2.67 (s) and 2.83 (s)(3H), 2.8–3.2 (2H, m), 3.6–3.7 (1H, m), 3.7–4.0 (4H, m), 4.2–5.0 (4H, m), 4.9–5.2 (1H, m), 5.01 (1H, d, J=3 Hz), 6.9–7.4 (11H, m), 7.50 (1H, d, J=8 Hz), 7.89 (1H, br s), 8.05 (1H, d, J=8 Hz), 8.3–8.5 (1H, m)

(6) IR (Nujol) : 3430, 3270, 3100, 1655, 1635, 1605, 1570, 1535, 1510 cm$^{-1}$

NMR (DMSO-d$_6$, δ): 1.7–1.9 (1H, m), 1.9–2.1 (1H, m), 2.70 (s) and 2.81 (s)(3H), 2.8–3.1 (2H, m), 3.6–3.7 (1H, m), 3.7–4.0 (4H, m), 4.2–4.6 (3H, m), 4.6–4.8 (1H, m), 4.8–5.1 (1H, m), 5.02 (1H, d, J=3 Hz), 6.9–7.4 (11H, m), 7.49 (1H, d, J=8 Hz), 7.90 (1H, br s), 8.06 (1H, d, J=8 Hz), 8.3–8.5 (1H, m)

(7) mp: 187°–88° C.

IR (Nujol): 3350, 3270, 1685, 1650, 1590, 1545, 1450, 1250 cm$^{-1}$

NMR (DMSO-d$_6$, δ): 1.7–1.9 (1H, m), 1.9–2.1 (1H, m), 2.7–3.1 (5H, m), 3.6–3.8 and 3.8–4.0 (2H, m), 3.86 (3H, s), 4.2–4.5 (3H, m), 4.6–4.8 (1H, m), 4.9–5.1 (2H, m), 6.9–7.3 (11H, m), 7.4–7.5 (1H, m), 7.8–8.0 (1H, m), 8.0–8.1 (1H, m), 8.3–8.5 (1H, m)

(8) IR (Nujol) : 3360, 1685, 1655, 1580, 1565, 1530 cm$^{-1}$

NMR (DMSO-d$_6$, δ): 1.6–1.8 (1H, m), 1.8–2.1 (1H, m), 2.71 (s) and 2.85 (s)(3H), 2.8–3.3 (2H, m), 3.6–3.7 (1H, m), 3.7–4.0 (1H, m), 3.86 (3H, s), 4.2–4.7 (4H, m), 4.8–5.1 (1H, m), 5.00 (1H, d, J=3 Hz), 6.9–7.3 (7H, m), 7.3–7.7 (5H, m), 7.89 (1H, broad s), 8.05 (1H, d, J=8 Hz), 8.3–8.6 (1H, m)

(9) mp: 172°–173° C.

IR (Nujol): 3430, 3280, 1655, 1630–1600, 1510, 1450, 1235 cm$^{-1}$

NMR (DMSO-d$_6$, δ): 1.7–1.9 (1H, m), 1.9–2.1 (1H, m), 2.7–3.0 (5H, m), 3.6–3.8 (1H, m), 3.69 (3H, s), 3.8–4.0 (1H, m), 3.85 (3H, s), 4.3–4.6, 4.6–4.8 and 4.8–5.1 (6H, m), 6.7–6.8, 6.9–7.3 and 7.5–7.6 (12H, m), 7.8–8.0 and 8.0–8.1 (2H, m), 8.3–8.5 (1H, m)

EXAMPLE 3

To a suspended mixture of Starting Compound (1.0 g) in methylene chloride (25 ml) was added pyridine (0.65 g) and cinnamoyl chloride (0.343 g) under ice-cooling. Tetrahydrofuran (5 ml) was added to the mixture and the resulting solution was stirred at the same temperature for one and half an hour and at room temperature for two hours. After concentration, the product was extracted with ethyl acetate and the organic layer was washed successively with diluted sodium hydrogen carbonate solution, water, 0.5N hydrochloric acid, and sodium chloride solution, and was dried with magnesium sulfate. After concentration, the residue was crystallized with a mixed solvent of ethyl acetate, diisopropyl ether, and ether, and was filtered and washed with diisopropyl ether to give Object Compound (1.13 g).

mp: 91°–94° C.

IR (Nujol): 3350 (sh), 3290, 1665, 1645, 1610, 1585, 1530 $cm^{-1}$

EXAMPLE 4

To an ice-cooled solution of Starting Compound (1.61 g) and BSA (1.89 g) in methylene chloride (35 ml) was added indole-3-carbonyl chloride (0.70 g). The solution was stirred at this temperature for two hours. To the evaporated residue was added a mixture of THF (20 ml) and water (5 ml). The mixture was stirred at room temperature for 20 minutes. The solution was washed with water, diluted sodium hydrogencarbonate solution, 0.5N hydrochloric acid and sodium chloride solution and dried over magnesium sulfate. After concentration, the residue was applied to a silica gel (42 g) column and eluted firstly with chloroform and secondly with chloroform-methanol (100:1:5 to 100:2 gradient elution) to give Object Compound (1.89 g).

IR (Nujol): 3250, 1750, 1630, 1510 $cm^{-1}$

NMR (DMSO-$d_6$, δ): 1.20 (3H, t, J=7 Hz), 1.7–2.1 (2H, m), 2.65–3.0 (5H, m), 3.6–3.7 and 3.8–4.0 (2H, m), 4.15 (2H, q, J=7 Hz), 4.2–4.5 (3H, m), 4.69 (2H, s), 4.7 (1H, m), 4.8–5.0 (2H, m), 6.7–6.8 (2H, m), 7.0–7.5 (10H, m), 7.85 (1H, br s), 8.03 (1H, d, J=7.3 Hz), 8.4 (1H, m), 11.64 (1H, br s)

EXAMPLE 5

The object compound was obtained according to similar manners to those of Preparation 15 and Example 1, successively.

IR (Nujol) : 3340, 1635, 1600, 1530 $cm^{-1}$

NMR (DMSO-$d_6$, δ): 1.7 (s) and 2.83 (s)(3H), 2.9–3.2 (2H, m), 3.86 (3H, s), 4.3–4.8 (4H, m), 4.8–5.1 (1H, m), 5.3–5.4 (1H, m), 5.6–5.7 (1H, m), 6.0–6.1 (1H, m), 6.9–7.6 (12H, m), 7.99 (1H, br s), 8.16 (1H, d, J=8 Hz), 8.5–8.7 (1H, m)

EXAMPLE 6

To an ice-cooled solution of Starting Compound (727 mg) in ethanol (15 ml) was added a solution of 1N sodium hydroxide (2.57 ml). The solution was stirred at room temperature for 3 hours. After evaporation of alcohol, water was added and the solution was lyophilized to give Object Compound (660 mg) as a powder.

IR (Nujol) : 3200, 1610, 1515 $cm^{-1}$

NMR (DMSO-$d_6$, δ): 1.8–2.1 (2H, m), 2.7–3.0 (including singlets at 2.72 and 2.85) (5H, m), 3.55–3.65 and 3.7–3.9 (2H, m), 4.13 (2H, s), 4.2 (1H, m), 4.4–4.6 (including singlet at 4.44)(2H), 4.68 (1H, m), 4.89 (1H, m), 5.24 (1H, s), 6.6–7.4 (11H, m), 7.49 (1H, d, J=7 Hz), 7.8 (1H, br s), 8.02 (1H, d, J=7 Hz), 8.31 (1H, m)

EXAMPLE 7

Starting Compound (0.6 g) was dissolved in methanol (40 ml) and hydrogenated over 10% palladium on charcoal (0.06 g) under atmospheric pressure for an hour. The catalyst was filtered off and the filtrate was concentrated to give Object Compound (0.61 g) as an amorphous solid.

IR (CHCl$_3$) : 3360, 1630, 1530, 1515, 1470, 1435, 1370, 1250 $cm^{-1}$

NMR (DMSO-$d_6$, δ): 1.7–1.9 (1H, m), 1.9–2.1 (1H, m), 2.6–2.9 (5H, m), 3.6–3.7 (1H, m), 3.85 (3H, s), 3.8–4.0 (1H, m), 4.3–4.5 (3H, m), 4.6–5.1 (5H, m), 6.4–6.5, 6.7–7.1, 7.1–7.3 and 7.4–7.5 (12H, m), 7.8–8.0 (1H, m), 8.0–8.1 (1H, m), 8.3–8.4 (1H, m)

EXAMPLE 8

Starting Compound (0.6 g) was dissolved in tetrahydrofuran (6 ml). To the solution was added 4N-HCl/DOX (0.28 ml) under ice-cooling. The solution was stirred for ten minutes and concentrated. The residue was triturated with ether and filtered and dried (40° C., 6 hours) to give Object Compound (0.58 g). mp:>173° C. (dec.)

IR (Nujol) : 3500–3100, 1630, 1530, 1510, 1250 $cm^{-1}$

NMR (DMSO-$d_6$, δ): 1.7–1.9 (1H, m), 1.9–2.1 (1H, m), 2.7–3.2 (5H, m), 3.6–3.7 (1H, m), 3.8–4.2 (4H, m), 7.0–7.6 (12H, m), 7.91 (1H, s), 8.06 (1H, d, J=7 Hz), 8.3–8.6 (1H, m), 4.2–5.1 (6H, m), 10.3 (3H, br s)

EXAMPLE 9

The object compound was obtained according to a similar manner to that of Example 1.

mp:>105° C. (dec.)

IR (Nujol): 3430–3280, 1645–1630, 1605, 1530, 1415 $cm^{-1}$

NMR (DMSO-$d_6$, δ): 1.75–1.95 (1H, m), 2.0–2.2 (7H, m), 2.70–2.78 (3H, s), 2.8–3.05 (2H, m), 3.6–4.0 (2H, m), 3.85 (3H, s), 4.25–5.05 (6H, m), 6.75–7.5 (11H, m), 7.8–8.1 (2H, m), 8.3–8.5 (1H, m)

EXAMPLE 10

The object compound was obtained according to a similar manner to that of Example 1.

IR (CHCl$_3$): 3300, 1660, 1650, 1460–1420 $cm^{-1}$

NMR (DMSO-$d_6$, δ): 1.7–2.25 (8H, m), 2.6–3.1 (5H, m), 3.5–3.9 (2H, m), 4.25–5.2 (6H, m), 6.8–7.6 and 7.95–9.0 (15H, m)

EXAMPLE 11

The object compound was obtained according to a similar manner to that of Example 8.

mp:>145° C. (dec.)

IR (Nujol) : 3270, 1690, 1660, 1580, 1565 $cm^{-1}$

NMR (DMSO-$d_6$, δ): 1.9–2.25 (8H, m), 2.6–3.1 (5H, m), 3.6–3.9 (2H, m), 4.25–5.15 (6H, m), 6.7–8.0 and 8.4–9.3 (15H, m)

EXAMPLE 12

To an ice-cooled solution of 1-methylindole-3-carboxylic acid (0.25 g) in methylene chloride (10 ml) were added successively TEA (0.22 ml) and pivaloyl chloride (0.19 ml).

The resulting solution was stirred for 25 minutes at the same temperature (Solution I).

Starting Compound (0.70 g) was distributed between methylene chloride and aqueous sodium hydrogencarbonate solution. The organic layer was separated and dried over magnesium sulfate, and concentrated to 5 ml volume.

This solution was added to Solution (I) prepared above, and the resulting solution was stirred over night, during which period the temperature was gradually raised to room temperature. To the solution was added N,N-dimethyl-1,3-propanediamine (0.044 ml) and the mixture was stirred for 40 minutes. After concentration, the residue was extracted with ethyl acetate. The organic layer was washed successively with an aqueous sodium hydrogencarbonate solution, water, 0.5N-hydrochloric acid and saturated aqueous sodium chloride solution, and dried over magnesium sulfate, and then concentrated in vacuo. This crude product was purified by silica gel column chromatography with a mixed solvent of chloroform and methanol (methanol concentration from 0.5% to 5%) as an eluent to give Object Compound as an amorphous solid (0.72 g).

IR (Nujol) : 3330, 1640–1630, 1530, 740 cm$^{-1}$

NMR (DMSO-d$_6$, δ): 1.60–2.10 (2H, m), 2.60–3.10 (5H, m), 3.86 (3H, s), 3.55–4.00 (2H, m), 4.20–5.10 (6H, m), 6.95–7.60, 7.80–8.55 (14H, m) MASS : M$^+$: 607

EXAMPLE 13

An ice-cooled solution of Starting Compound (1.25 g) in methylene chloride (6.8 ml) was treated with TFA (5.1 ml) for 40 minutes. After concentration, methylene chloride and sodium hydrogen carbonate solution were added, and the organic layer was separated and was washed with sodium chloride solution, and was dried over sodium sulfate. This solution was concentrated to 16 ml volume (Solution I).

To an ice-cooled solution of 1-methylindole-3-carboxylic acid (350 mg) in methylene chloride (15 ml) were added TEA (202 mg) and pivaloyl chloride (241 mg). This solution was stirred for 20 minutes at the same temperature and to this solution was added the solution prepared above (Solution I). The resulting solution was stirred for 2 hours at room temperature. After concentration, ethyl acetate and water were added and the separated organic layer was washed successively with sodium hydrogen carbonate solution, water, 0.5N hydrochloric acid, and sodium chloride solution, and was dried over magnesium sulfate. After concentration, the crude product was purified on a silica gel chromatography (24 g) eluting with a mixed solvent of chloroform and methanol (methanol 2%–2.5%) to give a purified product (0.95 g), which was crystallized by an addition of ethyl acetate. The crystals were collected by filtration, washed with diisopropyl ether, and dried to give Object Compound (0.72 g).

mp: 204°–205° C.

IR (Nujol): 3410, 1640, 1590, 1525 cm$^{-1}$

NMR (DMSO-d$_6$, δ) : 1.6–2.2 (2H, m), 2.08 and 2.14 (6H, s), 2.55–2.9 (4H, m), 3.0–3.4 (4H, m), 3.6–4.05 (5H, m), 4.3–4.6 (3H, m), 4.95–5.15 (2H, m), 5.4–5.6 (1H, m), 6.85–7.3 (10H, m), 7.5 (1H, m), 7.9–8.15 (2H, m)

EXAMPLE 14

To an ice-cooled solution of 3-(3,4-dimethoxyphenyl)-propionic acid (0.28 g) and HOBT (0.18 g) in methylene chloride (10 ml) was added WSC-HCl (0.26 g). The resulting solution was stirred for 2.5 hours at the same temperature (Solution I).

To an ice-cooled solution of Starting Compound (0.70 g) in methylene chloride (10 ml) was added TEA (0.20 ml). The solution was stirred for 1.5 hours at the same temperature. This solution was added to Solution I prepared above at the same temperature and the resulting solution was stirred overnight at room temperature. After concentration, the residue was extracted with ethyl acetate and the organic layer was washed successively with aqueous sodium hydrogen carbonate solution, water, 0.5N-hydrochloric acid and saturated sodium chloride solution, and dried over magnesium sulfate. After concentration, diisopropyl ether was added to the residue and the resulting precipitates were collected by filtration, and dried to give Object Compound as an amorphous solid (0.53 g).

IR (CHCl$_3$): 3300, 2940, 1630, 1512 cm$^{-1}$

NMR (DMSO-d$_6$, δ): 1.65–2.45 (2H, m); 2.06, 2.13, 2.18 (6H, s); 2.55–3.20 (6H, m); 2.74, 2.78, 2.81 (3H, s); 3.15–3.90 (2H, m); 3.67, 3.69, 3.70, 3.72, 3.73 (6H, s); 4.15–5.15 (6H, m);

6.55–7.40 (11H, m); 8.25–8.40, 8.60–8.80 (1H, m)

MASS: M$^+$: 601

EXAMPLE 15

The object compound was obtained according to a similar manner to that of Example 13.

NMR (DMSO-d$_6$, δ): 1.5–2.0 (2H, m), 2.14 (6H, s), 2.7–2.9 (9H, m), 3.12 and 3.16 (3H, s), 3.6–4.0 (4H, m), 4.3–4.6 (3H, m), 4.73 (2H, brS), 5.1 (1H, m), 5.5 (1H, m), 6.87–7.3 (10H, m), 7.7 (1H, m), 8.05 (2H, m), 10.91 (1H, brS)

MASS: M$^+$517

EXAMPLE 16

The object compound was obtained according to a similar manner to that of Example 1.

IR (Nujol) : 3300, 1630, 1565 cm$^{-1}$

NMR (DMSO-d$_6$, δ): 1.85–2.15 (2H, m), 2.15–3.10 (2H, m), 2.76, 2.77 and 2.89 (3H, s), 3.60–5.20 (8H, m), 6.85–7.80 (13H, m), 8.50–8.80 (1H, m)

MASS: M$^+$594

EXAMPLE 17

The object compound was obtained according to a similar manner to that of Example 14.

m.p.: 137°–139° C.

IR (Nujol) : 3400, 3250, 3100, 1630, 1570, 1420 cm$^{-1}$

NMR (DMSO-d$_6$, δ) : 1.7–1.9 (1H, m), four singlet at 2.05, 2.10, 2.11 and 2.17 (6H), 2.2–2.4 (1H, m), four singlets at 2.60, 2.64, 2.73 and 2.79 (3H), 2.8–3.05 (2H, m), 3.6–4.1 (2H, m), 4.3–5.2 (6H, m), 6.6–7.8 (14H, m), 8.54 and 8.73 (1H, d, J=8 Hz)

MASS: M$^+$553

What we claim is:

1. A compound of the formula:

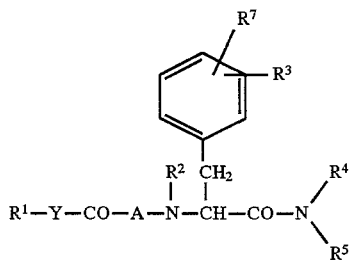

wherein $R^1$ is a group of the formula

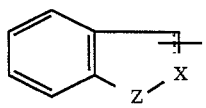

wherein the symbol of a line and a dotted line represent a single bond and X is $CH_2$ or NH, or said line and dotted line represent a double bond and X is CH or N, Z is O, S or N—$R^6$, wherein $R^6$ is hydrogen, lower alkyl, or N,N-di(lower)alkylamino(lower)alkyl;

$R^2$ is hydrogen or lower alkyl;

$R^3$ is lower alkyl, carboxy(lower)alkyl, esterified carboxy(lower)alkyl, carbamoyl(lower)alkyl, lower alkylamino(lower)alkyl, hydroxy(lower)alkyl, acyloxy(lower)alkyl, halo(lower)alkyl, carboxy(lower)alkoxy, esterified carboxy(lower)alkoxy, halogen, lower alkoxy, nitro, amino, or an acylated amino group;

$R^4$ is lower alkyl, carboxy(lower)alkyl or esterified carboxy(lower)alkyl, and $R^5$ is ar(lower)alkyl selected from the group consisting of mono-, di- and triphenyl(lower)alkyl or pyridyl(lower)alkyl, or

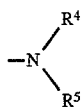

represents a heterocyclic moiety selected from the group consisting of 1-indolinyl, 2-isoindolinyl, 1, 2, 3, 4-tetrahydroquinolin-1-yl and 1, 2, 3, 4-tetrahydroisoquinolin-2-yl;

$R^7$ is hydrogen, lower alkyl, carboxy(lower)alkyl, esterified carboxy(lower)alkyl, carbamoyl(lower)alkyl, lower alkylamino(lower)alkyl, hydroxy(lower)alkyl, acyloxy(lower)alkyl, halo(lower)alkyl carboxy(lower)alkoxy, esterified carboxy(lower)alkoxy, halogen, lower alkoxy, nitro, amino, or an acylated amino group;

A represents an amino acid residue, wherein said amino acid is selected from the group consisting of D- or L-proline, D- or L-didehydroproline, D- or L-hydroxyproline, and D- or L-mercaptoproline, wherein if said amino acid is hydroxyproline or mercaptoproline, the amino acid side chain is optionally substituted with a moiety selected from the group consisting of lower alkanoyl, lower alkoxycarbonyl, trihalo(lower)alkoxy-carbonyl, $C_6$-$C_{10}$ar(lower)alkoxycarbonyl, lower alkylsulfonyl, lower alkoxyalyl, $C_6$-$C_{10}$arylsulfonyl, halo $C_6$-$C_{10}$ar(lower)-alkoxycarbonyl, carboxy(lower)alkanoyl, glycyl, β-alanyl, N-lower alkoxycarbonylglycyl, N-lower alkoxycarbonyl-β-alanyl, N,N-di(lower)alkylamino-(lower)alkanoyl, carboxyalyl, morpholino-carbonyl, amino(lower)alkanoyl, N-$C_6$-$C_{10}$ar(lower)alkoxycarbonyl-amino(lower)alkanoyl, threonyl, N-lower alkoxycarbonyl-threonyl, N-lower alkanoylthreonyl, N-lower alkoxycarbonyl(lower)alkyl-N-lower alkoxycarbonylamino-(lower)alkanoyl, α-glutamyl, N-$C_6$-$C_{10}$ar(lower)alkoxycarbonyl-O-$C_6$-$C_{10}$ar(lower)alkyl-γ-glutamyl, lower alkyl, carboxy(lower)alkyl, esterified carboxy(lower)alkyl, morpholino, glycino amide, threonino amide, N'-glutamylamino, N-lower alkylamide, di(lower)alkylamino, $C_6$-$C_{10}$ar(lower)alkyl, trihalo(lower)alkyl and lower alkoxycarbonyl(lower)alkyl; and Y is a valence bond, lower alkylene or lower alkenylene; or a pharmaceutically acceptable salt thereof.

2. The compound of claim 1, wherein said heterocyclic moiety is 1-indolinyl, 2-isoindolinyl, 1,2, 3, 4-tetrahydroquinolin-1-yl or 1,2,3,4-tetrahydroisoquinolin-2-yl.

3. A compound of claim 1, wherein $R^1$ is benzofuryl;

or a group of the formula:

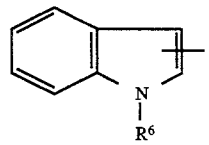

wherein $R^6$ is hydrogen;

lower alkyl; or

N,N-di(lower)alkylamino(lower)alkyl, $R^3$ is lower alkyl amino;

acylamino;

carboxy(lower)alkoxy;

esterified carboxy(lower)alkoxy;

halogen;

lower alkoxy; or nitro, $R^4$ is lower alkyl, $R^5$ is mono or di or triphenyl(lower)alkyl, $R^7$ is hydrogen; lower alkyl; or halogen;

A is hydroxyproline; or didehydroproline.

4. A compound of claim 2, wherein $R^1$ is benzofuryl, indolyl, 1-lower alkylindolyl or 1-N,N-di(lower)alkylamino-(lower)alkylindolyl, $R^3$ is lower alkyl, amino, lower, carboxy(lower)alkoxy, lower, halogen, lower alkoxy or nitro, $R^5$ is phenyl(lower)alkyl, and A is hydroxyproline or didehydroproline.

5. A compound of claim 4, wherein $R^1$ is benzofuryl, indolyl, 1-methylindolyl or 1-dimethylaminoethylindolyl, $R^2$ is hydrogen or methyl, $R^3$ is methyl, amino, carboxymethoxy, ethoxycarbonylmethoxy, fluoro, chloro, methoxy or nitro, $R^4$ is methyl, $R^5$ is benzyl, $R^7$ is hydrogen, methyl or chloro, and Y is a bond, ethylene or vinylene.

6. A compound selected from the group consisting of:

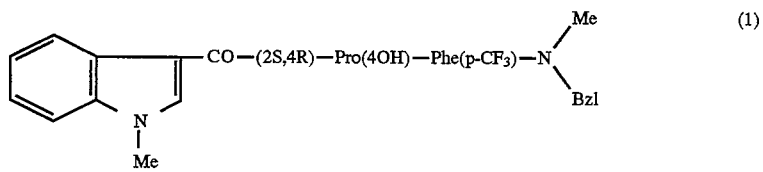 (1)
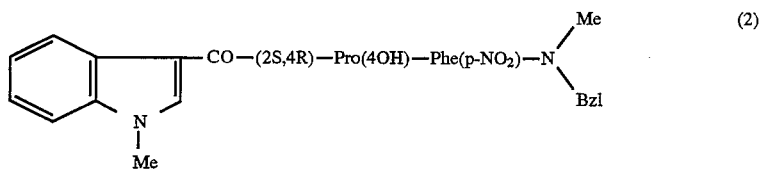 (2)
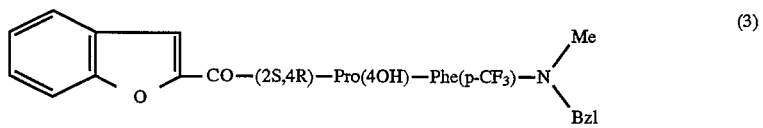 (3)
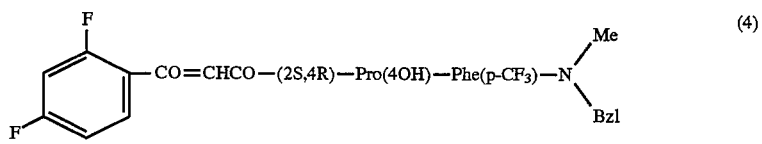 (4)
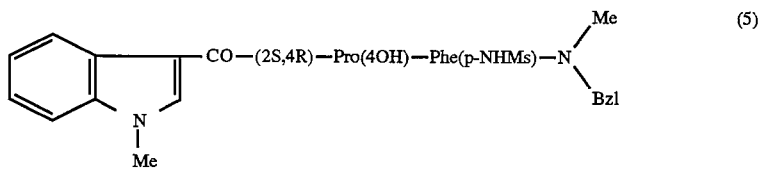 (5)
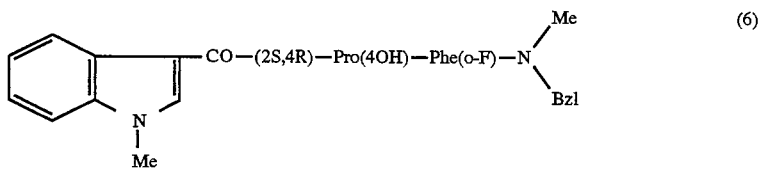 (6)
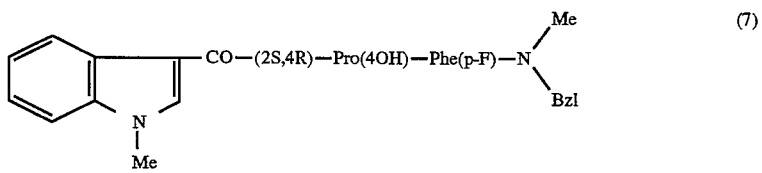 (7)
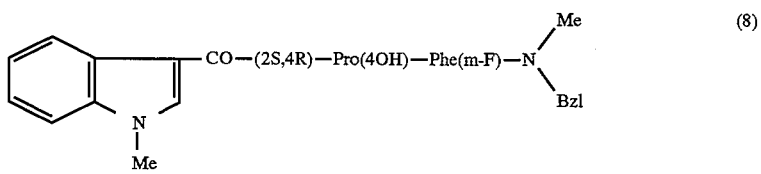 (8)
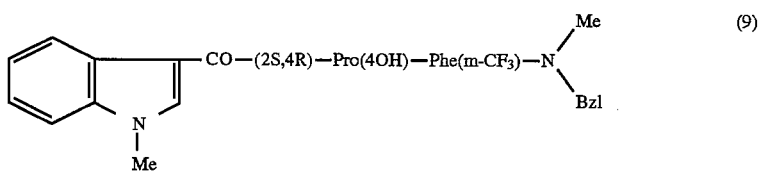 (9)

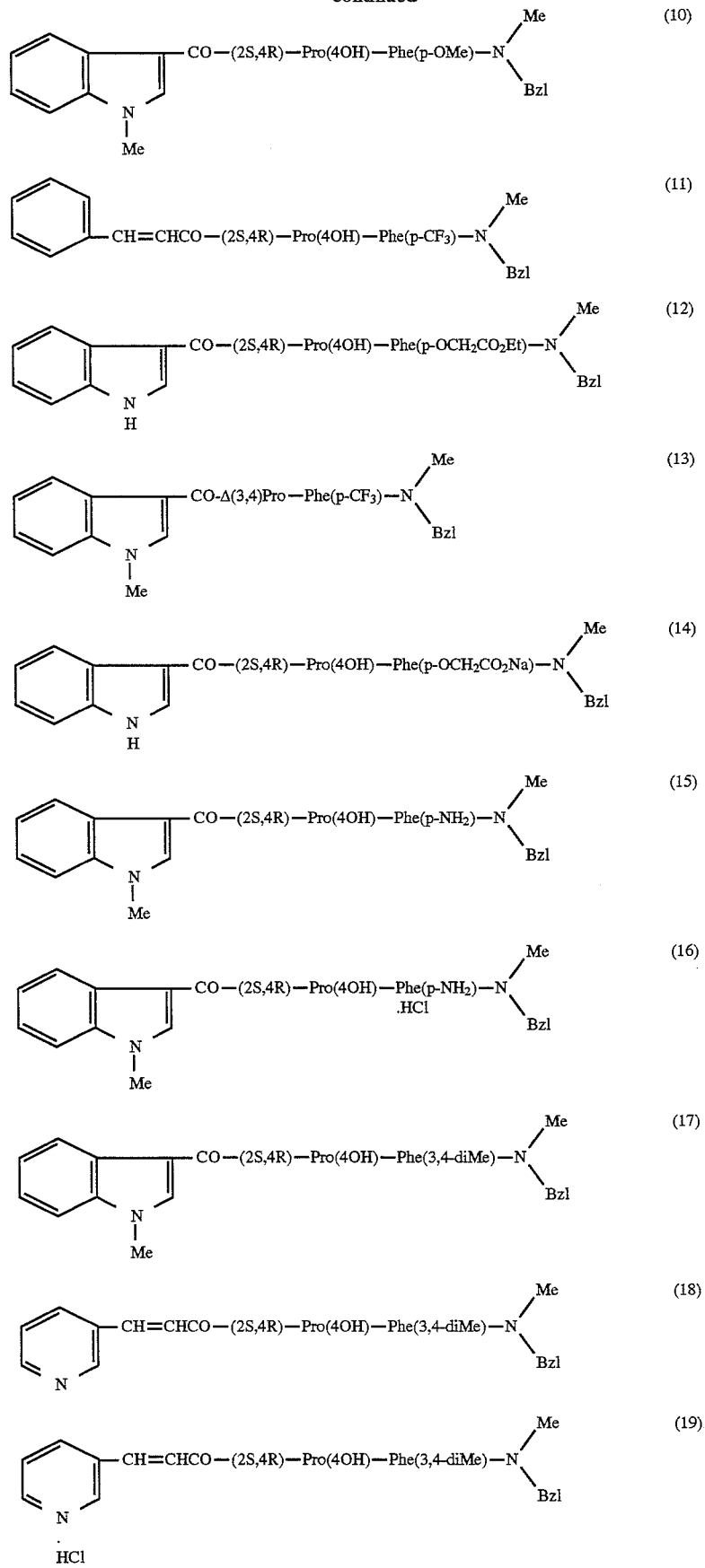

-continued

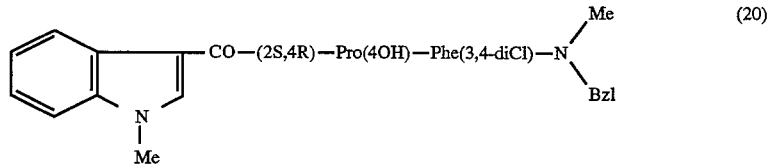
(20)

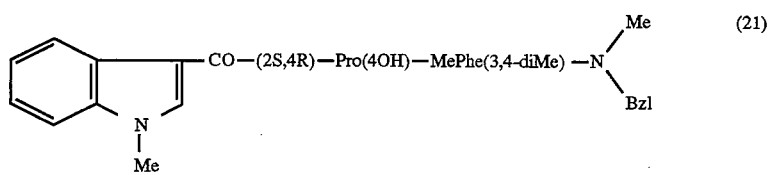
(21)

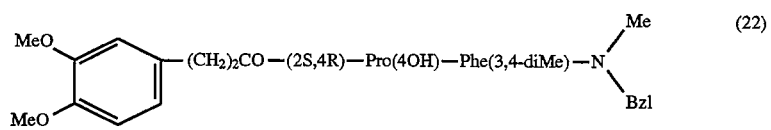
(22)

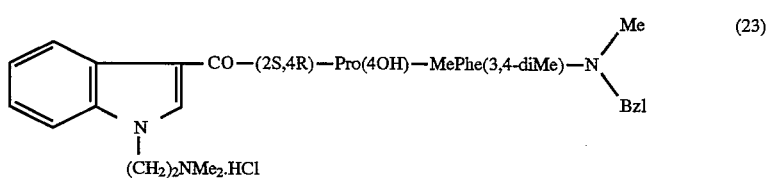
(23)

and

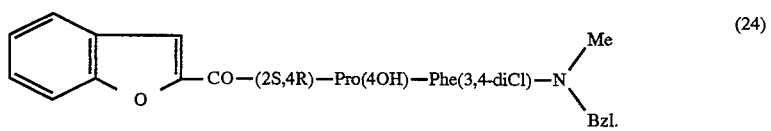
(24)

7. A compound of the formula:

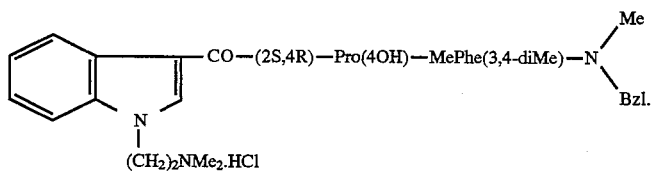

8. A compound of the formula:

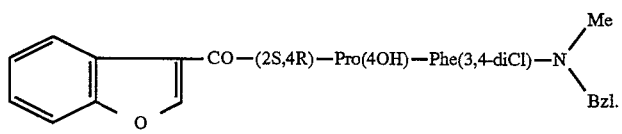

9. A pharmaceutical composition which comprises a compound of claim 1 and a pharmaceutically acceptable carrier or excipient.

10. A process for preparing a pharmaceutical composition which comprises admixing a compound of claim 1 with a pharmaceutically acceptable carrier or excipient.

11. A compound of claim 1 for use as a medicament.

12. A compound of claim 1 for use as a tachykinin antagonist.

13. A compound of claim 1 for use as a substance P antagonist.

14. A method for treating tachykinin mediated diseases selected from the group consisting of asthma, bronchitis, rhinitis, cough expectoration, conjunctivitis, vernal conjunctivitis, contact dermatitis, atopic dermatitis urticaria, rheumatoid arthritis, osteoarthritis, migraine, headache, toothache, cancerous pain and back pain, comprising administering the compound of claim 1 to a.human or animal in need thereof.

* * * * *